(12) United States Patent
Curry

(10) Patent No.: US 9,460,431 B2
(45) Date of Patent: *Oct. 4, 2016

(54) CONDITION STATUS-BASED DEVICE SYSTEM AND OPERATION

(71) Applicant: Patrick J. Curry, McGregor, TX (US)

(72) Inventor: Patrick J. Curry, McGregor, TX (US)

(73) Assignee: PJC Investments, LLC, Waco, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/800,810

(22) Filed: Mar. 13, 2013

(65) Prior Publication Data

US 2014/0247109 A1 Sep. 4, 2014

Related U.S. Application Data

(63) Continuation-in-part of application No. 13/784,387, filed on Mar. 4, 2013.

(51) Int. Cl.
| | | |
|---|---|---|
| *G05B 19/00* | (2006.01) | |
| *G05B 23/02* | (2006.01) | |
| *G05B 23/00* | (2006.01) | |
| *G06Q 40/00* | (2012.01) | |
| *G06Q 20/32* | (2012.01) | |
| *G06Q 10/00* | (2012.01) | |
| *G06Q 30/06* | (2012.01) | |
| *G07F 17/00* | (2006.01) | |

(52) U.S. Cl.
CPC .............. *G06Q 20/32* (2013.01); *G06Q 10/00* (2013.01); *G06Q 20/322* (2013.01); *G06Q 30/0601* (2013.01); *G07F 17/0057* (2013.01); *A61M 2205/3592* (2013.01)

(58) Field of Classification Search
CPC ...... G05B 1/01; H03C 3/0933; H03C 3/095; A61J 1/1437; A61J 2205/60; G06F 19/327; G06F 2221/2111; G06F 19/3406; A61B 5/002; A61B 5/1112; A61B 5/7475; A61B 5/0002; A61B 5/0022; H04L 67/125; H04L 67/025; B60R 2025/1016; B60R 25/33
USPC ............. 340/5.1, 3.1, 3.3, 539.12, 506, 426, 340/539, 993, 825.69, 5.21, 5.31, 5.8, 3.2, 340/10.34, 573.4, 5.81, 5.2; 700/90; 709/217, 223, 227, 250; 604/504, 503; 706/44; 235/379, 380

See application file for complete search history.

(56) References Cited

U.S. PATENT DOCUMENTS

| | | | |
|---|---|---|---|
| 5,588,038 A | * | 12/1996 | Snyder ............................ 340/7.1 |
| 6,124,805 A | | 9/2000 | Gabbard |
| 6,195,648 B1 | | 2/2001 | Simon et al. |
| 6,232,884 B1 | | 5/2001 | Gabbard |

(Continued)

OTHER PUBLICATIONS

U.S. Appl. No. 13/784,387, Non Final Office Action mailed Jul. 23, 2015, 43 pgs.

(Continued)

*Primary Examiner* — Mirza Alam
(74) *Attorney, Agent, or Firm* — Schwegman Lundberg & Woessner, P.A.

(57) ABSTRACT

A device, system or method may optionally include a processor, remote to a device, configured to generate information to control, at least in part, a function of the device based, at least in part, on a condition of conveyance of the device, and a transmitter, remote to the device, configured to transmit the information related to the condition of conveyance to the device.

20 Claims, 8 Drawing Sheets

(56) References Cited

U.S. PATENT DOCUMENTS

| | | |
|---|---|---|
| 6,400,155 B2 | 6/2002 | Kormos et al. |
| 6,408,330 B1 * | 6/2002 | DeLaHuerga ........ A61J 1/1437 709/217 |
| 6,411,217 B1 | 6/2002 | Gabbard |
| 7,266,507 B2 | 9/2007 | Simon et al. |
| 2004/0102683 A1 * | 5/2004 | Khanuja et al. .............. 600/300 |
| 2004/0176978 A1 * | 9/2004 | Simon ................ B60R 25/2018 705/35 |
| 2005/0192557 A1 * | 9/2005 | Brauker ............... A61B 5/0002 604/503 |
| 2006/0227987 A1 | 10/2006 | Hasler |
| 2007/0100514 A1 * | 5/2007 | Park ................................ 701/2 |
| 2007/0109117 A1 * | 5/2007 | Heitzmann ........... H04L 67/125 340/539.12 |
| 2009/0300507 A1 | 12/2009 | Raghavan et al. |
| 2012/0066155 A1 | 3/2012 | Garratt et al. |
| 2013/0090625 A1 * | 4/2013 | Moberg ............... G06F 19/3406 604/504 |

OTHER PUBLICATIONS

U.S. Appl. No. 13/784,387 Examiner Interview Summary mailed Aug. 20, 2015, 12 pgs.

* cited by examiner

CONDITION STATUS-BASED DEVICE SYSTEM AND OPERATION

PRIORITY

This application is a continuation-in-part under 35 U.S.C. 120 of U.S. patent application Ser. No. 13/784,387, Curry, filed Mar. 4, 2013, which is incorporated by reference herein in its entirety.

TECHNICAL FIELD

The disclosure herein relates generally to the operation of a device based on a non-operational condition status and methods therefor.

BACKGROUND ART

Various electrically-active devices, such as medical devices, consumer electronics, appliances, vehicles, machinery, and the like, are actively configurable and controllable in terms of features and functionality. Rather than simply being configured to be powered on and off, such as with a mechanical switch, such electrically-active devices may be electrically configured for various modes of operation. Such devices have been sold or otherwise conveyed to customers based on terms of sale, such as installment payment, lease, maintenance or service contracts, and the like.

DESCRIPTION OF THE EMBODIMENTS

Figure 1:
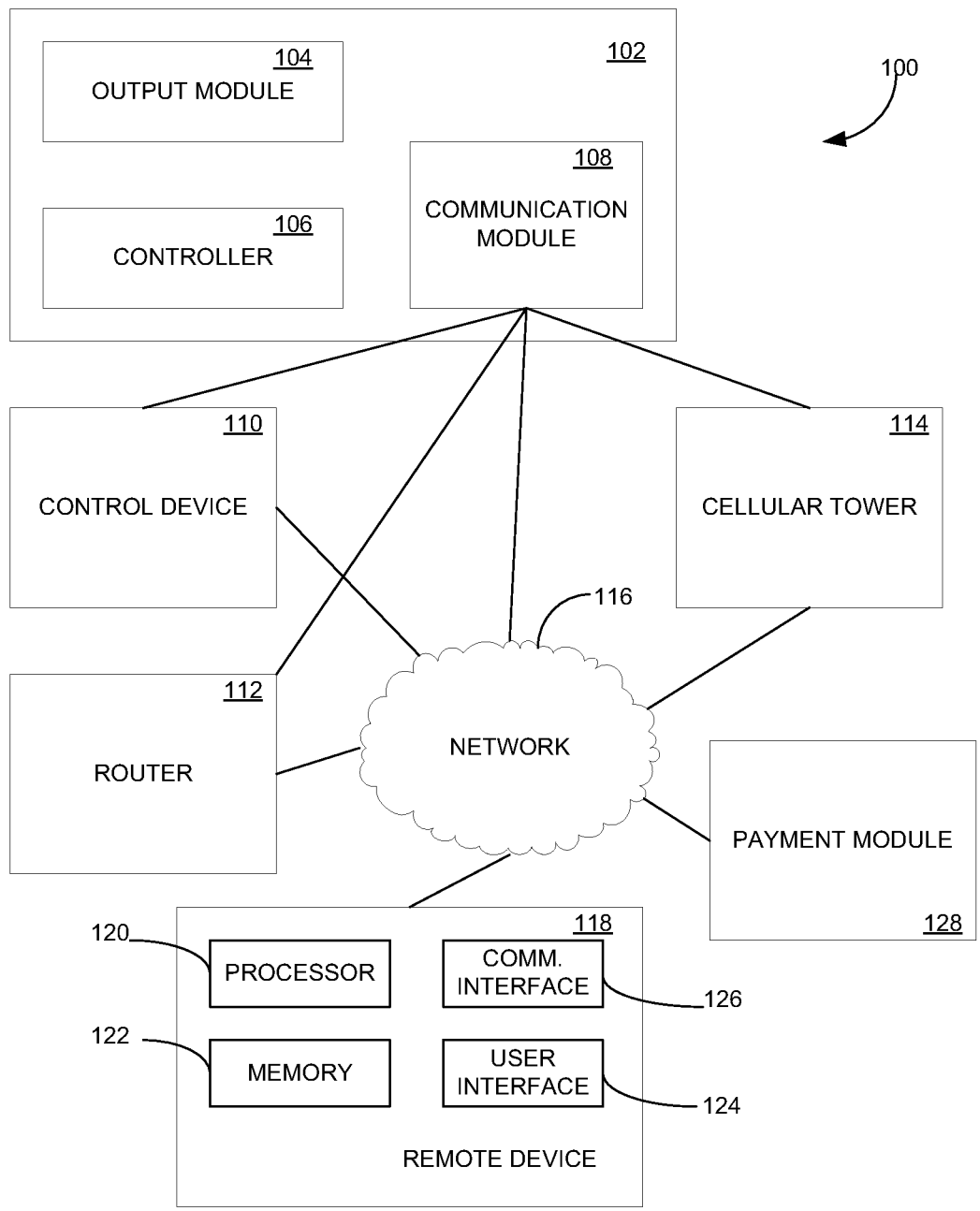
FIG. 1 is a block diagram of a system.

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments. Embodiments set forth in the claims encompass all available equivalents of those claims.

Conventionally, devices that are conveyed to a party acquiring the device or use of the device may be subject to legal enforcement of the terms of conveyance. If an acquiring party defaults on installment or lease payments or does not abide by maintenance requirements, for instance, the conveyor of the device may seek legal recourse, such as repossession of the device or damages. However, such legal recourse may be time consuming and/or expensive. Furthermore, if the acquiring party is unreachable, the acquiring party may maintain possession of the device notwithstanding the legal recourse of the conveyor of the device.

Electrical commands for controlling or configuring a device may be received local to the device, such as by directly, physically interacting with the device, or via a remote communication link, such as via wireless and/or networked communication modalities. For instance, a manufacturer or seller of a device could electrically configure a device to utilize or not utilize different functions based on an initial sale price. A seller of the device could engage or disengage various functions dependent on buyer need and willingness to pay for various functions at the time of sale or conveyance.

In contrast to the above circumstances of initially configuring a device, electrical control of a device may be based on a buyer or other user of the device meeting or having met a particular condition, such as a condition of conveyance. A conveyance may be any process by which the device is deliberately conveyed from a conveying party to an acquiring party, such as by sale, lease, loan, gift, and so forth. Electrical control of the device may be remote to the device, with information and commands based on the condition transmitted to and from the device via a network or other long-distance communication modality. On the basis of the acquirer or a subsequent user of the device having met the condition, such as a condition of conveyance, a condition status of the device may be utilized to control a function of the device, such as by disabling or enabling certain or all device functions. Thus, an acquirer of the device may not benefit from the device if the condition is not met without the party managing the device, such as they conveyor of the device, necessarily being able to find or directly obtain the device.

With respect to conditions of conveyance, it is to be understood that the condition of conveyance may be limited to provisions of an actual conveyance. Such conditions may be explicitly agreed upon by the parties to a contract for sale, lease, loan, transfer, etc. Alternatively or additionally, the conditions may be agreed on informally or may be compelled under law. Thus, a condition of conveyance may include, without limitation, a sale price and terms by which payments are made, a term of lease or subscription, maintenance requirements, follow up requirements, limitations on use, such as performance restrictions and geographic restrictions, and so forth.

It is noted that control of the device may be independent of the possessor of the device. In other words, it may not be the possessor that controls the device (such as by disabling or impairing a function of the device if the device is stolen) but rather the counterparty (or the counterparty's agent, assignee, or successor) in the transaction by which the possessor or original acquirer obtained the device. A condition of conveyance may not cover circumstances in which the conveyor or acquirer of the device may wish the device to be controlled but which does not actually violate a condition of conveyance. Thus, if a third party steals the device from the acquirer, the system disclosed herein may not disable or impair the device on the grounds of a condition of conveyance having been violated, because theft by a third party may not be a violation of a condition of conveyance.

Medical devices, for instance, may further be controlled on the basis of a non-physiologic condition of the patient. An example of a non-physiologic condition status of the medical device is the ongoing payment of an installment plan or fees by the patient utilizing the medical device and/or by the patient's insurance provider or other source of medical payments. For instance, a medical device may be sold to a patient on an installment plan or provided to a patient based, in essence, on a lease plan or a maintenance or subscription basis. The payments may be based on a binary, on/off operation of the medical device or on a functional basis, providing greater functional access to the patient in exchange for higher payments. To the extent that the payments are paid or not paid, or are increased or decreased, the patient may be warned of a change in functionality of the medical device, the medical device may be turned on or off, or the medical device may be utilized with greater or fewer functions. The medical device may operate based on a countdown clock that, unless the clock is interrupted upon payment having been received, may automatically adjust device functionality. Alternatively, the medical device may operate based on active control of device functionality by a local or remote source.

Further condition statuses are contemplated for a variety of devices, including, but not limited to, a follow up or maintenance status of the various devices. Various devices known in the art may require maintenance procedures, such as on a regular basis, in order to function safely and effectively and to reduce a likelihood of damage to the device itself. By way of example, if the oil is not changed in an automobile engine the engine may be irreparably damaged. Particularly in cases where the automobile is leased, the lessor may bear the cost of some or all of the resultant damage to the engine that may result from a lessee failing to implement required maintenance. Even in circumstances in which a maintenance requirement is not a part of a condition of conveyance, it may be in the best interest of various devices to be disabled or impaired in the event that maintenance records indicate a deficiency. In various examples, where a condition of the automobile, such as from the condition of conveyance, i.e., the lease, requires that scheduled maintenance occur, and information indicates that the lessee did not follow perform a mandated maintenance procedure according to a maintenance schedule, the system disclosed herein may reduce a likelihood of damage to the engine by reducing or disabling functionality of the automobile. Functions disabled or impaired may pertain directly to the unperformed maintenance procedure; in an example, if engine oil is not changed then the engine may be disabled or impaired while allowing other functions of the automobile, such as the audio system, to continue to function.

In various examples, a user may have scheduled and/or periodic follow up or maintenance procedures with a professional or sales representative of the device. In various examples, the user may be prompted or reminded to conduct the follow up procedure. Upon the lapsing of a time period related to the periodic or scheduled follow up procedure, functions of the device may be disabled or impaired, such as to protect the device from damage, until and unless the possessor of the device attends the follow up session and the follow up session is registered. Consequently, disabling the function of the device may be based not on actual damage to the device but on a failure of the possessor of the device to abide by required maintenance and/or follow up procedures without respect to an actual functional status of the device.

As detailed herein, the condition status of various devices may be discussed with respect to the payment status of the device. However, it is to be understood that references to payment status herein may apply to a condition status and, in various cases, a condition of conveyance, in general. Thus, a particular description of a payment status may be understood to any condition status as would be apparent under the circumstances.

Further, it is to be understood that the principles disclosed herein may apply to a variety of circumstances of conveyance of the device from a conveyor to an acquirer. The device may be sold, leased, loaned, given as a gift, or any other form of conveyance from a conveyor to an acquirer, such as a conveyor in privity with an acquirer. To the extent that any one example refers, for instance, to a buyer of a device, it is to be understood that the principles of purchasing a device based on conditions apply equally well to leasing, borrowing, or otherwise receiving a device based on conditions. To the extent that a third party acquires a device without a condition of conveyance, such as by theft from the acquirer, the system disclosed herein may not control functionality of the device for violation of a condition of conveyance, though, as noted above, it is to be understood that the system may provide for the disabling of functionality of the device for reasons other than the violation of a condition status.

FIG. 1 is a block diagram of an exemplary system 100 that includes a device 102. While devices generally may vary in function and structure, electrically active devices tend to have some form of output. For instance, medical devices may tend to have some form of medical or therapeutic output, some internal control over their operation, some communicative ability, and so forth. A consumer electronic device may output music, video, games, telephonic communication, and so forth. A vehicle may output motive force, and so forth. As a generic illustration, the device 102 is drawn to refer to those components and systems involved in generating the output as an output module 104.

The output module 104 may produce an output consistent with the functionality of the device 102. For instance, where the device 102 is a hearing aid, the output module 104 may output sound at a volume and frequency audible to the wearer of the hearing aid. Where the device 102 is a therapy delivery medical device, such as a pacemaker, defibrillator, neurological stimulator, drug pump, or the like, the output module 104 may be configured to deliver the corresponding therapy.

Alternatively, the device 102 may not include an output module 104, such as if the device 102 is a sensor. While the disclosure herein may relate specifically to adjusting the output from the output module 104, it is to be understood that other functions, such as sensing functions, of the device 102 may also be modified based on the condition status of the device 102, such as a conveyance condition status, as disclosed in detail herein.

It is to be understood that the condition status of a device 102 may be based on an output that derives, at least in part, from the internal function of the device 102 itself rather than as a platform for conveying content from another source. Thus, by way of example, a provider of media content, such as a cable television or satellite radio provider, may cut off delivery of the media content to a consumer electronic device of a customer who does not pay an associated bill. The control of functionality of the device 102 may not be based on the transmission of content to the device 102 or the ability of the device 102 to receive and display broadcast content but rather may be based on the native functionality of the device 102 itself. A condition status of the device 102 may thus be based on the possession and/or operation of the device itself rather than content provided to the device 102 or the ability of the device 102 to display or otherwise utilize the content.

The device 102 is further drawn to refer to those components and systems involved in controlling the device 102 as a controller 106. Additionally, the device 102 is drawn to refer to those components and systems involved in communicating with devices and systems outside of the device 102 as a communication module 108. The communication module 108 may be a conduit for any user or communicative interaction with the device 102 and may be as simple as an on/off switch or other direct user interface. While the output module 104, the controller 106, and the communication module 108 are drawn with specificity, it is to be understood that for a given device 102, specific elements may perform functions relevant to the output from the device, the control of the device, and communications involving the device, and thus, dependent upon various circumstances, may be understood as variously corresponding to or being assigned to the output module 104, the controller 106, and the communication module 108.

In various examples, the communication module 108 is a wired or wireless electrical interface configured to receive electronic signals. Where the interface is wired, the medical device 102 may be plugged directly into a port or other physical interface with a secondary control device 110 or router 112, or may be plugged into the control device 110 or router 112 via a wire or cable. Where the interface is wireless, an antenna may be utilized to communicate using various wireless modalities with an antenna on the control device 110, such as when using 802.11 WiFi or Bluetooth, to the router 112. The router 112 may, for instance, be a wireless router. The communication module 108 may additionally or instead communicate with a cellular tower 114, such as when using cellular communications, among various potential wireless destinations for communication from the device 102. While various exemplary communication modalities are mentioned herein, it is to be understood that any suitable communication modality known in the art may be utilized. For instance, the control device 110 may communicate with the device 102 via inductive communication, infrared communication, or relatively short range radio frequency (RF) communication.

The control device 110 may be a computing device or terminal in local proximity of the device 102 and may be configured to enable an operator to interface with and control the device 102. As detailed herein, the control device 110 may incorporate a user interface to permit the operator to display information related to and/or received from the medical device 102 and to input commands, such as may be utilized to control the device 102. The control device 110 may incorporate a communication interface such as may communicate with the communication module 108 of the device 102, such as by wired communication and/or wireless communication. The control device 110 may include further functions known in the art, such as by providing power to the device 102. In various examples, the control device 110 does not provide control functions for the device 102 and instead operates as a terminal for providing power and/or communication links to the device 102.

The control device 110, router 112 or cellular tower 114 may be connected to a network 116, such as the Internet. Additionally, the communication module 108 may be configured to communicate with the network 116 directly. A remote device 118 may likewise be connected to the network 116. The remote device 118 may be configured to communicate with the device 102 via the network 116 and, optionally, via the devices 110, 112, 114. The remote device 118 may be configured to obtain information from and/or transmit information to the device 102. The remote device 118 may be a computer or other computing device configured to enable a remote operator to interact in various ways with the device 102, such as by transmitting instructions to the device 102 and receiving data from the device 102, such as may be displayed to the operator on a user interface of the remote device 118. In various examples, the remote device 118 and other devices of the system 100 may communicate directly with the device 102 and without respect to a network 116, such as via a dialup connection, direct connection, connection via a local interfacing device such as in a store or office of a professional, such as a medical professional, a sales professional, a repair specialist, and so forth.

In various examples, a device of the system 100, such as one or more of the control device 110 and the remote device 118, may include proprietary and/or custom componentry configured to interface with the system 100 generally and execute actions related to such interactions as disclosed herein. Alternatively, the device 110, 118 may include conventional computing componentry that may be configurable or otherwise used to interface with the rest of the system. For instance, the remote device 118 may include a processor 120, a memory module 122, a user interface 124, and a communication interface 126, such as a wired modem or wireless transmitter and receiver. It is emphasized that the control device 110 may optionally include a processor 120, memory module 122, user interface 124, and communication interface 126 in addition to or instead of the remote device 118, or that the processor 120, memory module 122, user interface 124, and/or communication interface 126 may be associated with another device of the system 100 and not the control device 110 or remote device 118. The processor 120 may perform computations related to obtaining and utilizing payment status and identifying functions provided by the device 102 that may be enabled, disabled, or impaired based on the payment status. The memory module 122 may include electronic storage as disclosed herein and may store payment information, such as a payment status, and other electronic data pertinent to the operation of the device 118 and the system 100 generally. The user interface 124 may display information, such as a payment status, payment information generally, or messages related to payment status and medical device 102 function generally, as disclosed herein. The user interface 124 may also, in various examples, be utilized to receive payments, as disclosed herein. The communication interface 126 may communicate with the network 116 or with other members of the system 100 directly.

The system 100 may optionally further include a payment module 128. In a more general example, the payment module 128 may be a condition status module. As illustrated, the payment module 128 is coupled to the network 116 and, as a result, may be communicatively coupled to other devices that are coupled to the network 116, directly or indirectly, including the medical device 102. In various examples, the payment module 128 is directly coupled to, is an organic component of, or is divided between various components of the system 100, including but not limited to the device 102, the control device 110, and the remote device 118. The payment module 128 may be configured to accept payment for functions performed by the device 102, specifically, and the system 100, generally. To accept payment, the payment module 128 may be configured with a user interface to input payment information, such as a screen, a keyboard, a credit card scanner, and other user interface devices known in the art. While the payment module 128 is drawn with specificity, it is to be understood that for a given system 100, specific elements may perform functions relevant to obtaining information related to the payment status of the device 102 and thus, dependent upon various circumstances, be assigned to the payment module 128.

Where the payment module 128 is a more general "condition module," the condition module may be sensitive, for instance, to a maintenance status or a follow up status of the device 102. In an example, the condition module may obtain follow up information, such as that a follow up procedure has occurred or is overdue, in the same general manner as the payment module 128 receives payment information regarding the device 102. Based on the follow up information, the condition module or other devices within the system 100 may transmit or otherwise generate a condition status, such as a follow up status, to be utilized by the rest of the system 100 in the same manner as the payment status disclosed herein.

It is to be emphasized and understood that the payment module 128 as an identifiable entity is an optional component of the system 100. Further, the payment module 128 need not accept payment directly but may obtain payment information, such as information that a payment has been made, from a source outside of the system 100. In such an example, the payment module 128 may merely be a component of a device 110, 118 that communicatively interfaces with a source outside of the system 100, such as a bank or other financial institution or facilitator, to obtain payment information related to the device 102 and provide the payment information within or throughout the system 100. For instance, the payment module 128 may utilize computer componentry of the one or more devices 110, 118 to receive payments or payment information, such as payment status. For instance, the user interface 124 may be utilized to enter a credit card number or authorize an electronic payment, while the memory 122 may be utilized to store the payment information. Consequently, the payment module 128 may be a program or routine implemented on the hardware of a device, such as the control device 110 and/or the remote device 118, within the system 100.

The components of the system 100, including but not limited to the device 102, may be located within various specific devices and various specific housings. For instance, the device 102 may be contained within multiple discrete devices or may be a single device contained within multiple housings with the ability to communicate between devices and housings, as appropriate. Thus, in an example, the output module 104 may be located in a first housing while the controller 106 and the communication module 108 may be located in a second housing that is communicatively coupled to the first housing. Further, as noted above, as the functionality of the output module 104, the controller 106, and the communication module 108 may include various components and systems of the device 102, one or more of the output module 104, the controller 106, and the communication module 108 may be split between various housings or devices that together comprise or contain the device 102.

Figure 2:
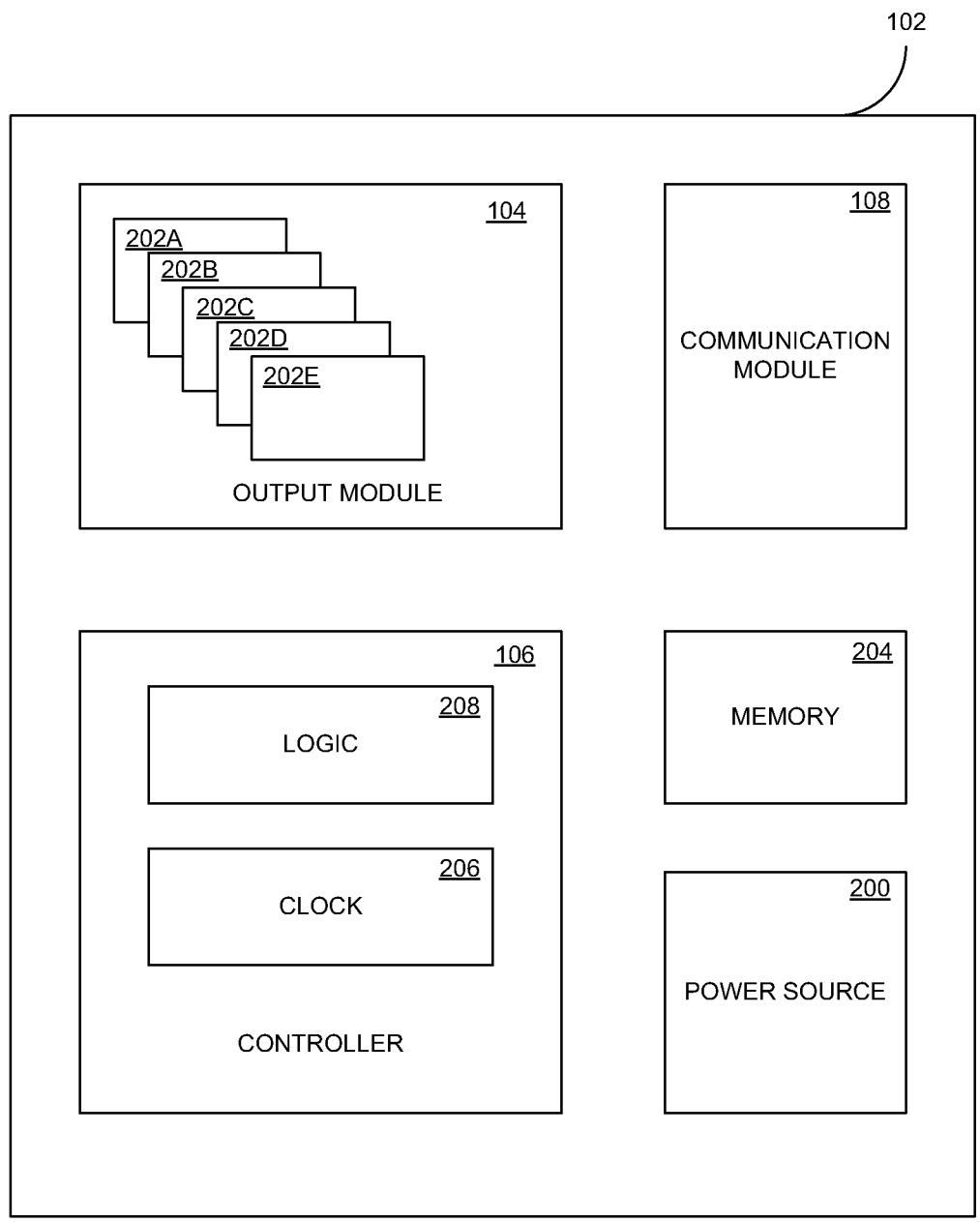
FIG. 2 is a block diagram of a medical device.

FIG. 2 is a detailed block diagram of an example of the device 102. In the illustrated example, the medical device 102 further includes a power source 200. The power source 200 may be a battery, such as a rechargeable battery, or other power source, such as a rechargeable power source, for instance a super capacitor. Alternatively, the power source 200 may derive power from a wall outlet or other external power source.

The output module 104 includes multiple functions 202A-E. While five functions 202 are illustrated, in various examples the number of functions may be more or fewer as appropriate. Each of the functions 202A-E is configured to deliver a different output or contribute collectively to a common output. For instance, where the device 102 is a hearing aid, one function 202A may provide audio amplification to a detected audio signal while another function 202B may provide audio filtering to the same signal, and so forth.

A further illustrative example includes where the device 102 is an appliance, such as a refrigerator. One function 202A may provide basic refrigeration, another function 202B may provide temperature monitoring and response, another function 202C may provide ice and drinking water at an external port, and so forth. Another illustrative example may include where the device 102 is an automobile. One function 202A may provide basic driving functionality, another function 202B may provide the automobile's audio system, another function 202C may provide power window control, and another function 202D may provide heating and cooling, and so forth. Consequently, in certain examples, various functions 202 may be incorporated or removed from an overall output function to provide different levels and characteristics of output from the output module 104.

A memory module 204 may be configured to provide volatile and/or non-volatile data storage. The memory module 204 may incorporate random access memory (RAM), flash memory, read-only memory (ROM), and other memory and data storage systems, both fixed and removable, as well known in the art. The memory module 204 may be a component of the controller 106, such as by being cache memory, may be separate from the controller 106, or may be partially incorporated in the controller and partially separate. The memory module 204 may store, among other data, a payment status of the device 102. It is emphasized that the memory module 204 may not be included and that, for instance, storage of a payment status of the device 102 may occur elsewhere in the system 100, such as in the control device 110 or the remote device 118.

In an example, the controller 106 incorporates or, in an alternative example, accesses a system clock 206. The controller 106 may further incorporate a logic module 208. The logic module 208 may include logic based on conditions by which functions 202 may be added or removed from active operation based on a payment status of the device 102.

In various examples, during or upon manufacture, a manufacturer of the device 102 may configure the functions 202 to place the device 102 into a certain configuration. The device 102 may be configured for low functionality, such as by selecting just one function 202, and initially sold at relatively low cost, or the device 102 may be configured for high functionality, such as by selecting most or all of the functions 202, and initially sold a relatively high cost. Conventionally and without respect to an ongoing payment status of the device 102, the device 102 may then operate based on the initially-selected functions 202 until the end of the device's 102 operational life.

The medical device 102 disclosed herein, however, further takes into account a condition status, such as a payment status, of the device 102, such as on an ongoing basis, in determining the functionality of the device 102. The payment status of the device 102 may be based on an amount that a payment should be and a schedule by which the payment should be made. For instance, a user of the device 102 may purchase the device 102 on an installment plan. Where the device 102 is a hearing aid, the user or purchaser may agree to a total price to be paid in scheduled, periodic installments over time. Whether or not those installments have been paid may, as is disclosed in detail herein, be utilized to determine overall device 102 functionality or particular functions that are performed by the device 102. For instance, as disclosed in detail herein, if an installment payment is missed, a consumer electronic device may be turned off or set to a lower level of functionality. In addition, if new functionality is desired from the consumer electronic device, a new installment payment may be made to enable the new functionality in the consumer electronic device.

In further examples, a user of the device 102 may lease the device 102, may enter into a maintenance agreement for the device 102 that includes periodic maintenance fees, or may enter into a subscription service for the device 102. Where, for instance, the device 102 is a hearing aid, the device 102 may provide functions 202 based on whether or not the periodic payment of the fee has been made or is in arrears. Consequently, a user of the hearing aid may continue making the payments for as long as the user desires to continue using the hearing aid and may cease making payments when the user no longer desires to use the hearing aid or no longer makes the payments.

The memory module 204 may store a time at which a payment is due to be paid. The time may be relative, such as one calendar month following making the pervious payment, or may be absolute, such as by a certain date and time. The controller 106 may compare the certain date and time against the time and date provided by the clock 206. Prior to the lapsing of the time period, the controller 106 may induce the output module 104 to deliver the selected functions 202 per normal or otherwise pre-set operating conditions, such as those for which the device 102 was configured upon manufacture. Upon the time lapsing, however, if the controller 106 has not been notified that the payment has been made, the controller 106 may induce the output module 104 to disable or impair some or all of the functions 202 or may disable or impair operation of the device 102 altogether, such as by disconnecting the power source 200 electrically or mechanically from the rest of the device 102.

Functions 202 may be disabled, entirely or essentially entirely, by terminating or otherwise blocking the function. Thus, the driving function of an automobile may be disabled either by terminating operation of the power train altogether or by preventing the transfer of motive power from the engine to the wheels, thereby preventing, in whole or in part, the automobile from moving under its own power. A function 202 may be impaired by limiting the ability of the function to perform at full capability. For instance, the driving function of an automobile may be impaired by limiting the top speed of the vehicle to less than its maximum or normal operating speed. Thus, an automobile with an impaired driving function may be limited to a top speed of, for instance, five (5) miles per hour or other limit as appropriate to the particular circumstances. Such principles may be readily applied to other functions and other devices.

The system 100 in general may allow for a "grace period" or an extension beyond the appointed payment time in which the payment may be paid without disabling functions 202. Alternatively, the functions 202 may be partially disabled or impaired during the grace period, such as by disabling individual functions 202 while leaving other functions 202 enabled. Alternatively or in addition, functions 202 may individually, progressively be disabled or impaired following the lapsing of the payment period. In an example, no functions 202 are disabled or impaired during the grace period. In an alternative example, individual functions 202A-E are progressively disabled or impaired during and/or after the grace period, though in certain examples basic functionality of the device 102 may be maintained during the grace period. In an example in which functions are not disabled or impaired during the grace period, subsequent disabling of functions 202 may be progressive or all at once and may be complete or partial.

It is noted that, upon making the payments, the device 102 may be reactivated even after operation of the device 102 has been disabled or impaired. In one example, disabling the operation of the device 102 for failure to meet scheduled payments does not disable or impair operation of the controller 106 and the communication module 108, through which a command may be received to reactivate operation of the device 102, such as by the control device 110 or the remote device 118, upon payment. In an alternative example, the device 102 may be entirely or essentially entirely powered off, upon which reactivation of the device 102 may occur on the basis of direct interaction with the device 102, such as by using a magnet to interact with a reed switch, cycling a mechanical switch on or within the device 102, interfacing the device 102 with an external port, such as on the control device 110, or other modes for reactivating the device 102.

The user of the device 102 or other party, such as a party authorized to act on the user's behalf, may make payments via the payment module 128. The payment module 128 may be configured to automatically withdraw the payment from an account at predetermined intervals or may receive the payment on an ad hoc basis, such as by receiving a credit card, specific account access authorization, or other payment vehicle. In an example, upon the payment module 128 receiving the payment corresponding to the device 102, the payment module 128 transmits a notification to the device 102 that the payment has been properly paid. The device 102 may store an indication that the payment has been paid in the memory module 204. The time for making the next payment may be extended from the time of receipt of the payment by a predetermined period of time, such as by setting the next date for receiving the payment one calendar month in the future. Alternatively, the date for receiving the payment may be extended by a predetermined time from the next due date. For instance, if the payment is made on the $13^{th}$ of the month but wasn't due until the $15^{th}$ of the month, the next due date for the payment may be the $15^{th}$ of the following month. Alternative payment scheduling is contemplated.

Depending on the nature of the device 102, various functions 202 may be disabled or impaired depending on the payment status while other functions 202 may be maintained notwithstanding the payment status. Control of such variable status may be maintained by the logic module 208. For instance, if the device 102 is a medical device and provides functionality critical for sustaining life, the logic module 208 may identify the functions 202 that are not essential to sustaining life that may be selectively disabled or impaired and functions 202 that are essential for sustaining life that may be maintained notwithstanding payments having been made. Thus, in the example of a pacemaker, a function 202A that provides basic, life-sustaining pacing may be maintained while functions 202B-E that provide enhanced pacing functions may be disabled or impaired. The logic module 208 may factor in the nature of the device and a status of a patient condition. Thus, though the medical device 102 may be capable of providing life-sustaining therapy, if the patient is not in need of the life-sustaining therapy the function related to the life-sustaining therapy may be disabled or impaired. Certain medical devices 102, such as medical devices 102 that are not life-critical, may have all functions 202 disabled entirely upon lack of payment. Similarly or relatedly, devices 102 for which an immediate disabling or impairing of functionality may be potentially dangerous or overly disruptive, such as an automobile, may not have functionality disabled or impaired until the device 102 in question is not in use, such as where the engine is not running or the automobile is parked.

The logic module 208 may be updated with various conditions for disabling, or impairing, or maintaining functions based on payment status. For instance, if government regulations prohibit disabling or impairing certain device functions 202 based on failure to make payments, the logic module 208 may peremptorily block those functions 202 from being disabled or impaired. As government regulations evolve, the logic module 208 may be updated accordingly. The logic module 208 may further be updated based on policies from a company or professional that manages the maintenance of the medical device 102. If a function is to be provided or not provided to a user of the device 102 notwithstanding the payment status, the logic module 208 may be updated accordingly.

The logic module 208 and the system 100 generally may further incorporate graduated payments. For instance, a user of the device 102 who has a device enabled for certain functions 202A-C may decide that the function 202C is no longer desired while continuing to desire functions 202A-B. The user may optionally make a payment that corresponds to functions 202A-B while not making payments related to function 202C. Accordingly, the message transmitted from the payment module 108 to the device 102 may reflect that functions 202A-B have been paid for while function 202C has not. The logic module 208 may then direct that functions 202A-B remain enabled while directing that function 202C be disabled or impaired. If the user subsequently makes the payment for function 202C, the logic module 208 may direct that function 202C be re-enabled.

In a further example, the device 102 may initially be enabled with functions 202A-C on initial purchase, and an installment plan, a lease plan, or maintenance or subscription fee may include payments based on those enabled functions 202A-C. However, a user may additionally come to benefit from or desire an additional function 202D. The additional function 202D may be enabled and the periodic installment, lease, or maintenance payments related to the device 102 increased accordingly. As such, selecting or otherwise enabling new functionality may be understood as resulting in a new condition of conveyance or a modification to a previous condition of conveyance. In the example of a hearing aid, the hearing aid may not initially have a low frequency filter enabled at the time of the initial sale. After the initial sale, however, the user may desire low frequency filtering, upon which the low frequency filtering may be enabled and the installment payments increased based on the price of the low frequency filtering function. Similarly, a purchaser of an automobile may not live in or frequent a climate in which traction control is particularly needed, but may move to a climate in which such a function 202 is advantageous, whereupon the function 202 may be selected and payments increased accordingly.

Additionally, the system 100 generally may recognize that a user may benefit from a currently non-enabled function 202. In the above example related to low frequency filtering, the hearing aid may have been sold on the understanding that the user would not expect to be in environments with significant amounts of low frequency noise. However, the hearing aid may subsequently detect relatively significant amounts of low frequency noise upon use. Based on the detection of the low frequency noise and, in various examples, the transmittal of either the detected noise itself or a summary or profile of the detected noise out of the medical device 102, the system 100 may determine, such as with the medical device 102 itself, the control device 110, the remote device 118, or a combination thereof, that the user may benefit from low frequency filtering. The system 100 may then display a recommendation on the medical device 102, the control device 110, the remote device 118, or elsewhere recommending that low frequency filtering be enabled and providing an ongoing installment, lease, maintenance, or subscription payment that may be entered into in compensation for the increased functionality of the hearing aid.

Similarly, an automobile may be constructed with a traction control system that includes both the actual traction control output, as may be produced by the output module 104, and sensors that may identify when the traction control system should be engaged, such as when one or more wheels slips or skids. If the associated traction control function 202 is not enabled, the sensors related to the traction control function 202 may nevertheless obtain and store, such as in the memory module 204, information related to the traction control function 202, such as instances where the traction control function 202 would have been engaged if the function 202 had been enabled. On the basis of a number of times traction control would have been engaged or a frequency with which traction control would have been engaged, the system 100, such as the logic module 208 or the remote device 118, may present a recommendation that the traction control function 202 should be engaged, such as to the user of the automobile or to a sales representative.

In various installment plans, the purchaser of the device 102 may pay installments for particular features 202 as the features are enabled. Alternatively, the purchaser may pay installments on an "all-in" service, in which all functions 202 are available as needed for one payment amount. In such an example, not all functions 202 are necessarily enabled but rather may be selectively enabled as the system 100, a user, a sales associate, or other individual involved with the system 100 determine that the related functionality is needed by or useful to the user.

The system 100 generally may generate notifications of payment status to the user or other operators or users of the system 100. For instance, if the device 102 has the capacity to provide notices to the user, such as by verbal or non-verbal means, the device 102 may notify the user that a payment is coming due, is due, or has been missed and that various functions 202 have been or are being disabled or impaired until the payment is made. For instance, a hearing aid may output audio tones, such as a particular type of beep or sequence of beeps, to indicate that payment is due. Consumer electronic devices such as smartphones and the like may readily display such notices. Alternatively or additionally, notifications can be provided on user interfaces 124 of the control device 110, the remote device 118, or other devices that are connected to the system 100. The extensiveness of the notifications may vary based on the user interface 124 capabilities of the device on which the notifications are displayed. Thus, for instance, if the user interface 124 includes a conventional computer or tablet screen, relatively detailed notifications may be provided that include what payment is owed, when the payment is owed, and what functions 202 will be disabled or impaired if the payment is not made, among other information. If the user interface includes a very small screen or no screen at all the message may be short and/or perfunctory relating to a payment being due or overdue.

In various examples, the controller 106 monitors a time until a payment is due and, if an indication that the payment has been made is not received by that time, the controller 106 disables or impairs functions 202 as appropriate. In such an example, the payment module 128 transmits a message upon receiving the payment. In various examples, rather than waiting for a message to be received asynchronously, the controller 106 transmits a message to the payment module 128 requesting a payment status, to which the payment module 128 synchronously transmits a current status, e.g., that the payment has or has not been made. In such an example, then, the device 102 may perform the function of monitoring the passage of time and may actively prompt the payment module 128 for the status, in contrast with other examples in which the rest of the system 100 monitors the payment status and provides the payment status to the device 102. The device 102 may, for instance, notify the rest of the system 100 that payment is due by a particular date.

In further examples, the medical device 102 has no sensitivity to payment status. In such examples, the system 100, such as the control device 110 and/or the remote device 118, monitors the payment status for the medical device 102 and the functionality of the medical device 102 that is related to the payment status. In such a case, the control device 110 and/or remote device 118 may direct the medical device 102 to enable, disable, or impair particular functions 202 or to enable, disable, or impair the general functionality of the medical device 102 as a whole based on the payment status of the medical device 102. As such, the medical device 102 may have functionality information but not information related to the payment status.

In further examples, instructions relating to the payment status are not transmitted from the payment module 128 but rather from another component of the system, such as the control device 110 or the remote device 118. In such an example, the payment module 128 may communicate to the other device 110, 118 that the payment has not been made and that the medical device 102 may be subject to having functions 202 disabled or impaired. An operator of the device 110, 118 may be prompted to authorize or not authorize disabling or impairing some or all of the functions 202 to be disabled or impaired, or may otherwise be prompted to select functions 202 to be disabled or impaired. In one such non-limiting example, upon operator authorization of the disabling or impairing of functions 202 on the device 102 is a command transmitted to the device 102 directing that particular functions 202 are to be disabled or impaired. In one, non-limiting example, while the device 102 may or may not be sensitive to the passage of time and whether or not a payment is due, the command to disable or impair functions 202 may originate solely from outside of the device 102 and may, in various non-limiting examples, be transmitted upon an operator selection. In such an example, if the device 102 were to fall out of communication with the payment module 128 or other device 110, 118, the functions 202 may not be disabled or impaired while the medical device 102 is out of communication.

Examples that rely on or otherwise utilize monitoring the internal clock 206 of the device 102 may disable or impair functions 202 upon the lapsing of the payment time period if the device 102 cannot or does not establish communication contact with the rest of the system 100. In such an example, the default condition for the device 102 may be to disable or impair functions 202 unless affirmative notice is given that the payment has not been made. In alternative examples, the default condition for the device 102 is that the payment has been made unless a payment status notification is provided that indicates that the payment has not been made. In such examples, the device 102 may continue to operate even if out of communication with the rest of the system 100.

In further examples, a device 102 may be purchased based on a payment that provides a predetermined duration of use for the device 102, upon which the device 102 shuts down. By way of example, though a device 102 may have a useful life of ten (10) years, the device 102 may be rented for a two (2) year period, upon which the device 102 may be shut down and returned to the seller. In such an example, the functions 202 may be entirely turned off, partially turned off, and/or the power source 200 electrically disconnected from the rest of the device 102. Upon return to the seller, the device 102 may be turned on and/or re-enabled, such as by turning on functions 202 and/or reconnecting the power source 200.

As disclosed herein, disabling or impairing functions 202 specifically or the functionality of the device 102 generally has been described on the basis of electronic commands and does not necessarily permanently damage the device 102. The disabling or impairing of functions 202 specifically, and functionality of the device 102 generally, may be in such a way as to permanently disable or impair the functionality. For instance, electronic components may be deliberately destroyed by creating a short circuit in the device 102, or machine parts may be disabled or impaired by expelling lubricant from the device 102 so that the machine parts seize and fail.

Failure to meet a condition status for the device 102 may result in the enablement of various functions 202, such as may exceed the mere notification of a delinquency in the condition status of the device 102. For instance, a transponder function 202 may be enabled to facilitate locating the device 102. Alternatively or additionally, functions that make continued possession of the device 102 annoying or irritating may be enabled, such as unpleasant sounds, lights, and so forth.

The control of the functionality of the device 102 on the basis of a condition status of the device may be automatic or essentially automatic and may trace from the condition status and related information actually stored or input in the system 100. Thus, the mere remote control of a device, such as remotely turning a device on or off, would not be sensitive to a condition status or condition status information. Further, where the condition status is based on a condition of conveyance, merely remotely controlling the functionality of a device may not be based on failure to meet a condition of conveyance from a conveyor, such as willing conveyor, to a receiver of the device 102.

System

In various examples, the system 100 may be understood to be a system for monitoring payments for devices, such as the device 102 and others as may be communicatively coupled to components of the system 100, on an installment payment plan and for notifying users of late payments. In such an example, the device 102 may not be a component of the system 100 at all but rather may interface with the system 100 to provide and/or receive information regarding functions 202 and payment status. Such monitoring and notification may be on the basis of modes of operation disclosed herein. Consequently, a user of the system 100 may be an organization that provides services related to payment for and maintenance of devices without the user of the system 100 having any affiliation with the manufacture or marketing of the devices that may interface with the system 100.

In various examples, as noted herein, the remote device 118 is a computer, a server, or other computing device configured to receive payment information, such as from the payment module 128, and functionality information, such as from the device 102, the control device 110, or the remote device 118 itself. The remote device 118 may be utilized by a user of the system 100 to monitor and control the performance of any of a number of devices in the system. The remote device 118 may interface with devices 102, control devices, and so forth via the network 116 or via more direct communication modalities, such as are disclosed herein.

The system 100 as a whole may be utilized by a system operator to monitor payments and device functionality deriving therefrom. The system operator may, for instance, be a device distributor, an insurance provider, or a healthcare provider, such as a hospital or clinic or healthcare system. Consequently, operation of the system 100 and the control of the device 102 functions 202 may be by entities other than a manufacturer of the device 102 or an entity that programs or otherwise configures the device 102 in the first instance.

Hearing Aid Example

Figure 3:
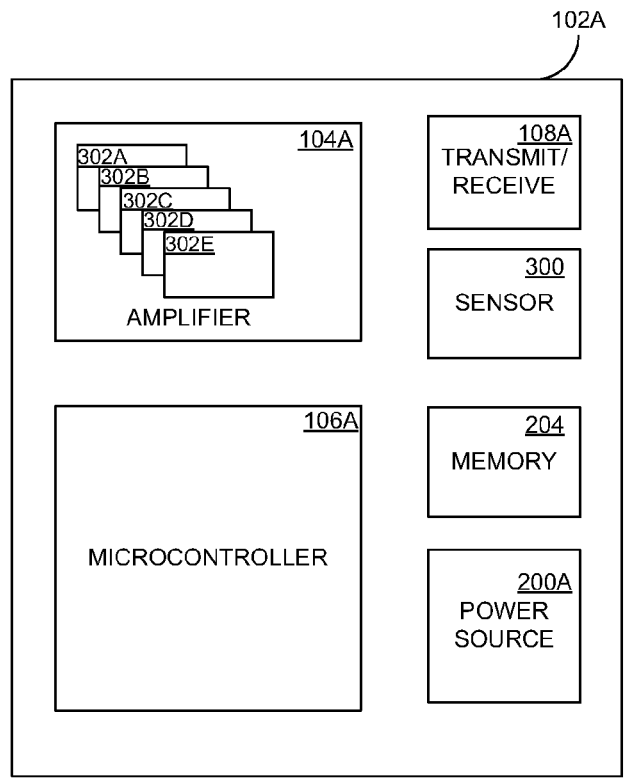
FIG. 3 is a block diagram of a hearing aid.

FIG. 3 is an example block diagram where the abstract components of the device 102 as depicted in FIGS. 1 and 2 are given exemplary detail. In the example, the device 102 is a hearing aid 102A. It is to be understood that the example provided here is not limiting and hearing aids may incorporate various components, systems, and functionality that is not necessarily specified here with particularity.

In such an example, the hearing aid 102A includes a sensor 300 that detects ambient noise, such as a microphone. An amplifier 104A (e.g., the output module 104) includes a speaker and componentry to amplify and/or filter the ambient noise as detected by the sensor 300. In various examples, a radio frequency transmitter/receiver 108A (e.g., the communication module 108) includes an antenna and transceiver configured to transmit and receive radio frequency communications by way of the antenna. In various examples, a microcontroller 106A and related componentry (e.g., the controller 106) is operatively coupled to the sensor 300, the amplifier 104A, and the radio frequency transmitter/receiver 108A. In various examples, the hearing aid 102A has a rechargeable battery 200A (e.g., the power source 200) and includes both volatile memory, such as RAM, and non-volatile memory, such as flash memory as the memory module 204.

In the example of the hearing aid 102A, the functions 302 include amplification 302A, a low frequency filter 302B, a high frequency filter 302C, a feedback filter 302D, and an environmental adjustment 302E function, among other functions that may be incorporated in a hearing aid 102A. In an exemplary use case, the user of the hearing aid 102A may purchase the hearing aid on an installment basis, such as equal quarterly installment payments for five years. In an example, the purchase of the hearing aid 102A entails a basic payment for the hearing aid 102A itself as well as amplification 302A. In an example, each of the functions 302B-E add incremental additional cost to the installment payment. In an example, each function 302B-E may increase the installment payment by the same amount. Alternatively, the installment cost of each function 302B-E may be set independently.

In an exemplary, non-limiting use case, the user of the hearing aid 102A selects functions 302B-D. Every quarter a payment module 128, and/or the system 100 in general, transmits a payment status to the hearing aid 102A. In the use case, for the first eight quarters the user pays the installment payment through the automatic withdrawal of funds from an account by the payment module 128. In each quarter, the payment module 128 transmits to the hearing aid 102A a payment status indicating that the installment payments are current and the microcontroller 106A directs the amplifier 104A to continue to deliver the functions 302A-D. Prior to each quarterly installment payment coming due, the amplifier 104A sounds a tone audible to the user of the hearing aid 102A indicating that the installment payment is about to be paid, and, in an example, another tone indicating that the installment payment has been successfully received.

However, in the ninth quarter the account includes insufficient funds to cover even the basic installment payment of the hearing aid 102A and amplification 302A. Consequently, the payment module 128 transmits a payment status to the hearing aid 102A indicating the hearing aid 102A is in arrears. In such an example condition, the microcontroller 106A directs the amplifier 104A to sound a tone to the user indicating that the payment status is in arrears and disable or impair all functions 302A-D, resulting in the hearing aid 102A becoming essentially non-functional to the user. In an example, the battery 200A may be electrically disconnected from the amplifier 104A, the microcontroller 106A, and the transmitter/receiver 108A, but in alternative examples the battery 200A may remain connected.

In the use case described above and herein, following the disabling or impairing of the function of the hearing aid 102A, sufficient funds are placed in the account from which the payment module 128 draws the funds for the installment payments for the hearing aid 102A. In an example, an operator of the system 100, such as via the remote device 118, initiates the payment module 128 to check the status of funds in the account. Alternatively, the payment module 128 periodically checks the status of funds in the account if the payment status is in arrears.

Upon determining that sufficient funds are in the account, the payment module 128, and/or the system 100 generally, transmits a payment status to the hearing aid 102A, such as via the transmitter/receiver 108A if the battery 200A has not been disconnected. Upon receiving the payment status, the microcontroller 106A commands the amplifier 104A to enable the functions 302A-D. Quarterly installment payments are then obtained by the payment module 128 and payment status updates are provided to the hearing aid 102A.

Pacemaker Example

Figure 4:
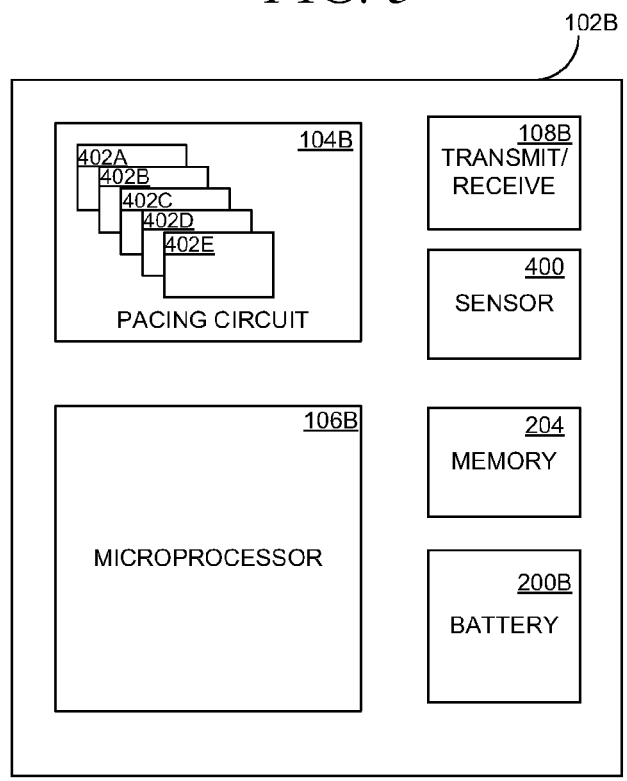
FIG. 4 is a block diagram of a pacemaker.

FIG. 4 is an example block diagram where the abstract components of the device 102 as depicted in FIGS. 1 and 2 are given exemplary detail. In the example, the device 102 is a pacemaker 102B. It is to be understood that the example provided here is not limiting and pacemakers may incorporate various components, systems, and functionality that is not necessarily specified here with particularity.

In such an example, the pacemaker 102B includes a sensor package 400, such as that may, in various examples, detect a patient's heart rate, blood pressure, blood-oxygen levels, and so forth. A pacing delivery circuit 104B (e.g., the output module 104) includes circuitry to generate and deliver pacing pulses to the heart. In various examples, a radio frequency transmitter/receiver 108B (e.g., the communication module 108) includes an antenna and transceiver configured to transmit and receive radio frequency communications by way of the antenna. In various examples, a microprocessor 106B and related componentry (e.g., the controller 106) is operatively coupled to the sensor package 400, the pacing delivery circuit 104B, and the radio frequency transmitter/receiver 108B. In various examples, the pacemaker 102B has a battery 200B (e.g., the power source 200) and includes both volatile memory, such as RAM, and non-volatile memory, such as an electrically programmable read-only memory (EPROM) as the memory module 204. The control device 110 may be a physician programmer, such as may be found in a medical facility, or may be remote patient management device, such as may be found in a patient's home.

In the example of the pacemaker 102B, the functions 402 include ventricular pacing 402A, atrial pacing 402B, biventricular pacing 402C, rate adaptability 402D, and minute ventilation 402E, among other functions that may be incorporated in a pacemaker 102B. In an exemplary use case, the user of the pacemaker 102B may purchase the pacemaker on an installment basis, such as equal monthly installment payments for five years. In an example, the purchase of the pacemaker 102B entails a basic payment for the pacemaker 102B itself. In an example, each of the functions 402A-E add incremental additional cost to the installment payment. In an example, each function 402A-E may increase the installment payment by the same amount. Alternatively, the installment cost of each function 402A-E may be set independently.

In an exemplary, non-limiting use case, the user of the pacemaker 102B selects functions 402A, B, and D; the biventricular pacing function 402C is not enabled as the patient does not, at the time of purchase, suffer from congestive heart failure and thus may not benefit from biventricular pacing. Every month the pacemaker 102B transmits a message to the payment module 128 and the system 100 in general that a payment is due for the pacemaker 102B and functions 402A, B, and D. In the use case, for the first two years the user pays the installment payment through the automatic withdrawal of funds from an account by the payment module 128 with the payment module 128 responding to payment status queries from the pacemaker 102B that the payment status is up to date and not in arrears. In an example, the sensor 400, the microprocessor 106B, and/or the system 100 generally, then identifies that the patient has started suffering from congestive heart failure and that the patient is now indicated for biventricular pacing 402C. In an example, at least one of the control device 110 and the remote device 118 is provided with a notification that the patient is indicated for biventricular pacing and that the biventricular pacing function 402C may be enabled for an added installment payment. In an example, the patient or the patient's caregiver may select to enable the biventricular pacing function 402C, such as on the control device 110 or the remote device 118, the control device 110 or the remote device 118 may communicate with the pacemaker 102C, and the pacemaker 102C may start delivering the biventricular pacing 402C.

In the exemplary use case, two years later the installment payments for the pacemaker 102C fall into arrears. In an example, when the payments fall into arrears a message is transmitted, such as via the network 116, to the control device 110 to notify the patient or the patient's caregiver of the payment status. When the pacemaker 102C queries the payment module 128, the payment module 128 or the system 100 generally may notify the pacemaker 102C that the installment payment is in arrears. The microprocessor 106C may include the logic module 208 that may compare the payment status against policies, such as government regulations and company policies, and determine that the functions 402B-D may be properly disabled or impaired while the ventricular pacing function 402A may not be disabled or impaired. Accordingly, the microprocessor 106B may direct the pacing delivery circuit 104B to only deliver ventricular pacing 402A and disable or impair the other functions 402B-D. A message may be transmitted to the control device 110 or the remote device 118 notifying the patient that therapy has been modified and directing the patient to contact their medical professional or medical device 102B sales representative. In various examples, the medical professional or sales representative may disable or impair the ventricular pacing function 402A.

The pacemaker 102B may periodically, such as monthly, check the payment status by querying the payment module 128. If the payment module 128 replies that the payment status of the medical device 102B is no longer in arrears for some or all of the functions 402B-D, those functions may be 402B-D may be restored. The pacemaker 102B may suspend queries upon a lapsing of a predetermined period of time with the payment status in arrears, such as one year.

Drug Pump Example

Figure 5:
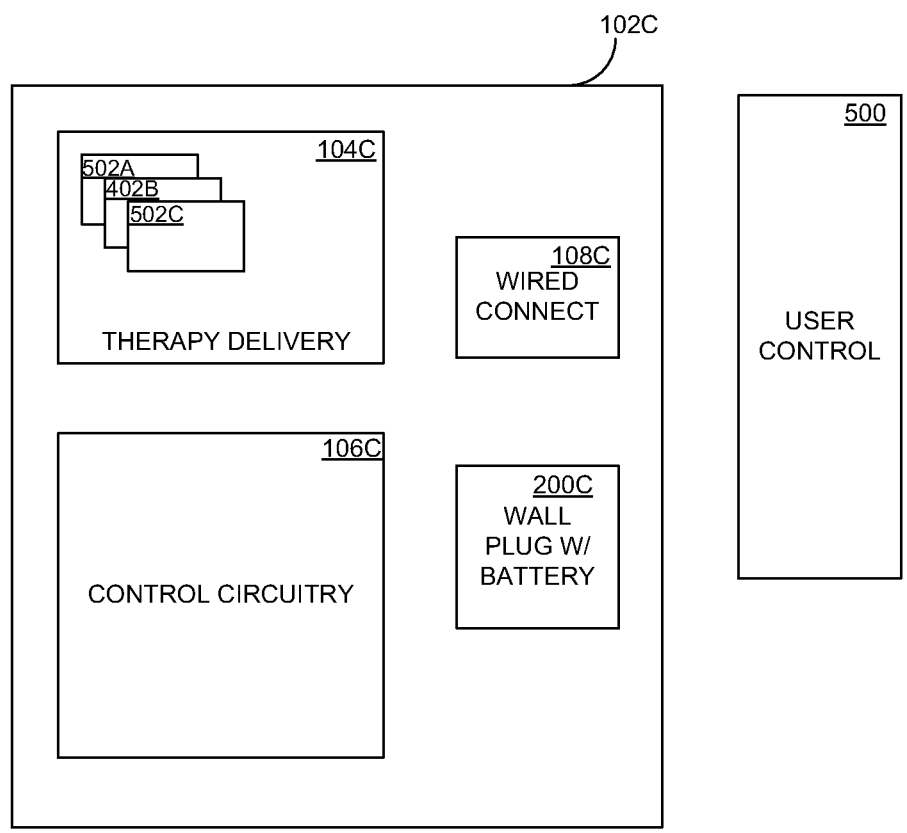
FIG. 5 is a block diagram of a drug pump.

FIG. 5 is an example block diagram where the abstract components of the device 102 as depicted in FIGS. 1 and 2 are given exemplary detail. In the example, the device 102 is a drug pump 102C. It is to be understood that the example provided here is not limiting and drug pumps may incorporate various components, systems, and functionality that is not necessarily specified here with particularity.

In such an example, the drug pump 102C includes a user control 500 that the user may use to adjust drug delivery levels, such as to deliver a bolus dose of a drug or other therapeutic substance (herein, the "drug"). As illustrated, the user control 500 is in a separate housing or a separate device from the drug pump 102C, though in various examples the user control 500 is a component on or within the same housing as the rest of the drug pump 102C. A therapy delivery system 104C (e.g., the output module 104) includes a reservoir for the drug and a pump and tubing to deliver the drug to a treatment location in the patient. In various examples, a wired connector 108C (e.g., the communication module 108) includes a port configured to be coupled to a communication cable that is operatively coupled to the control device 110. In various examples, control circuitry 106C, such as simple, narrowly-focused logic gates and related componentry (e.g., the controller 106) is operatively coupled to the therapy delivery system 104C, and the wired connector 108C. In various examples, the drug pump 102C has a wall plug with battery backup 200C (e.g., the power source 200).

In the example of the drug pump 102C, the functions 502 include basal rate drug delivery 502A, time sensitive basal rate drug delivery 502B (e.g., higher and lower basal rates dependent on a time of day or other relevant time consideration), and bolus drug delivery 502C, among other functions that may be incorporated in a drug pump 102C. In an exemplary use case, the user of the drug pump 102C may obtain the drug pump 102C via a maintenance payment schedule, such as equal annual installment payments for ten years. The maintenance payment schedule may provide for drug pump 102C functionality 502A as well as refills to the reservoir of the therapy system 104C. In an example, each of the functions 502B-C add incremental additional cost to the maintenance payment. In an example, each function 502B-C may increase the maintenance payment by the same amount. Alternatively, the installment cost of each function 502B-C may be set independently.

In an exemplary, non-limiting use case, the user of the drug pump 102C selects 502B for time-dependent basal rate drug delivery but not bolus drug delivery 502C. Every year the payment module 128 and/or the system 100 in general obtains payment via a credit card transaction. Based on the credit card transaction, the system 100 determines a payment status of the drug pump 102C and transmits a function command to the drug pump 102C allowing for the continued delivery of the functions 502A and B or disabling or impairing delivery of the functions 502A and B. In the use case, in the first year the user pays the maintenance payment through the payment module 128 with a credit card and the system 100 directs the drug pump 102C to continue to deliver functions 502A and B.

However, in the use case, after the first year the user decides bolus drug delivery functionality 502C is desirable. In such a case, a user of the system 100, such as via the control device 110, notes that additional functionality is desired and that the subsequent maintenance payment may be increased to reflect the maintenance cost of the bolus drug delivery function 502C. In an example, the function 502C may be immediately enabled. Alternatively, upon the payment of the following maintenance payment in full, the system 100 may transmit an instruction to the drug pump 102C to enable the bolus dose function 502C, whereupon the user may be able to command a bolus drug dose, such as with the user control 500.

It is to be emphasized and understood that the example use cases disclosed herein may be applied to any of a variety of medical devices 102, both in terms of the actions taken and the components utilized.

Follow Up Example

Further to the example illustrated with respect to FIG. 3, the hearing aid 102A may operate on a follow up status of the hearing aid 102A. It is to be understood that the example provided here is not limiting and hearing aids may incorporate various components, systems, and functionality that is not necessarily specified here with particularity.

In such an example, the hearing aid 102A includes a sensor 300 that detects ambient noise, such as a microphone. An amplifier 104A (e.g., the output module 104) includes a speaker and componentry to amplify and/or filter the ambient noise as detected by the sensor 300. In various examples, a radio frequency transmitter/receiver 108A (e.g., the communication module 108) includes an antenna and transceiver configured to transmit and receive radio frequency communications by way of the antenna. In various examples, a microcontroller 106A and related componentry (e.g., the controller 106) is operatively coupled to the sensor 300, the amplifier 104A, and the radio frequency transmitter/receiver 108A. In various examples, the hearing aid 102A has a rechargeable battery 200A (e.g., the power source 200) and includes both volatile memory, such as RAM, and non-volatile memory, such as flash memory as the memory module 204.

In the example of the hearing aid 102A, the functions 302 include amplification 302A, a low frequency filter 302B, a high frequency filter 302C, a feedback filter 302D, and an environmental adjustment 302E function, among other functions that may be incorporated in a hearing aid 102A. In an exemplary, non-limiting use case, the user of the hearing aid 102A selects functions 302B-D. In an example, the user is scheduled to have semiannual follow up procedures or checkups with a medical professional. Upon reaching a predetermined time prior to a scheduled follow up, such as one week, an audio message may be output by the amplifier 104A to remind the user to attend to the follow up session. The audio message may be a verbal message or may be beeps or other tones to indicate the follow up status.

Upon lapsing of the time period to conduct the follow up session, a further audio indication of the follow up status of the hearing aid 102A may be output by the output module 102A. Various individual functions 302 may be disabled or impaired, in an example one function every predetermined period of time, such as every one week. Thus, in the illustrated use case, in four weeks the hearing aid 102A may have no functionality at all owing to the progressive disabling or impairing of each of the four selected functions 302A-D.

In the use case described above and herein, following the disabling or impairing of at least one of the functions of the hearing aid 102A, the user attends a follow up session with a medical professional. The medical professional and/or the system 100 generally registers that the follow up session has occurred, and the condition module (as disclosed above, a general implementation of the payment module 128) may transmit a follow up status to the hearing aid 102A indicating that the hearing aid 102A is current on follow ups. Upon receiving the follow up status, the microcontroller 106A commands the amplifier 104A to enable the functions 302A-D.

Smartphone Example

Figure 6:
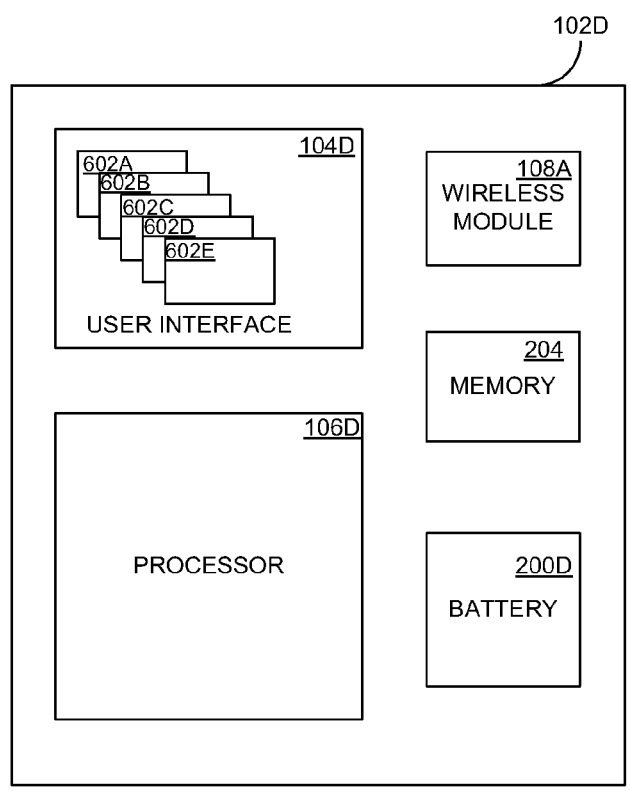
FIG. 6 is a block diagram of a smartphone.

FIG. 6 is an example block diagram where the abstract components of the device 102 as depicted in FIGS. 1 and 2 are given exemplary detail. In the example, the device 102 is a smartphone 102D. It is to be understood that the example provided here is not limiting and smartphones and other consumer electronic devices may incorporate various components, systems, and functionality that is not necessarily specified here with particularity.

In such an example, the smartphone 102D includes a user interface 104D (e.g., the output module 104) that includes a touchscreen, a microphone, a speaker, and/or audiovisual ports as well known in the art. In various examples, a wireless module 108D (e.g., the communication module 108) includes an antenna and transceiver configured to transmit and receive various examples of radio frequency communications, including, but not limited to cellular communications, WiFi, Bluetooth, and other modalities. In various examples, a processor 106D and related componentry (e.g., the controller 106) is operatively coupled to the user interface 140D, and the radio wireless module 108D. In various examples, the smartphone 102D has a rechargeable battery 200D (e.g., the power source 200) and includes both volatile memory, such as RAM, and non-volatile memory, such as flash memory, as the memory module 204.

In the example of the smartphone 102D, the functions 602 include cellular communication 602A, music output 602B, video output 602C, location services 602D, and third party applications 602F, among other functions that may be incorporated in a smartphone 102D. In an exemplary use case, the user of the smartphone 102D may purchase the smartphone 102D on a subscription basis, such as equal monthly subscription payments for five years. In an example, the condition of conveyance of the smartphone 102D entails a basic subscription payment for the smartphone 102D itself as well as cellular communication 602A. In an example, the subscription may be without respect to a plan with a cellular provider for actual communication via a cellular network; consequently, the continued enablement, disablement, or impairment of the cellular communication function 602A may be without respect even to the existence of a cellular plan for actually utilizing the cellular communication function 602A. In an example, each of the functions 602B-E add incremental additional cost to the subscription payment. In an example, each function 602B-E may increase the subscription payment by the same amount. Alternatively, the subscription cost of each function 602B-E may be set independently.

In an exemplary, non-limiting use case, the user of the smartphone 102D selects functions 602B-D. Every month a payment module 128, and/or the system 100 in general, transmits a payment status to the smartphone 102D. In the use case, for the three months the user pays the subscription payment through the automatic withdrawal of funds from an account by the payment module 128. In each month, the payment module 128 transmits to the smartphone 102D a payment status indicating that the subscription payments are current and the processor 106D directs the user interface 104D to continue to deliver the functions 602A-D. Prior to each monthly installment payment coming due, the user interface 104D displays a message indicating that the subscription payment is about to be paid, and, in an example, another message indicating that the subscription payment has been successfully received.

However, in the fourth month the account includes insufficient funds to cover even the basic subscription payment of the smartphone 102D and cellular communication 602A. Consequently, the payment module 128 transmits a payment status to the smartphone 102D indicating the smartphone 102D is in arrears. In such an example condition, the processor 106D directs the user interface 104A to display a message indicating that the payment status is in arrears and disable or impair all functions 302A-D, resulting in the smartphone 102D becoming essentially non-functional to the user.

In the use case described above and herein, following the disabling or impairing of the function of the smartphone 102D, the payment module 128 periodically checks for payments. In an example, three months pass without late payments being made. Upon the lapsing of the three month period without a payment status update indicating that the payment status is no longer in arrears, the processor 106D directs at least one circuit in the smartphone 102D, such as within the processor 106D, to close a short circuit and deliberately damage at least one system-critical electronic component in the smartphone 102D so as to render the smartphone 102D disabled or impaired without physical repairs being made to the smartphone 102D.

Automobile Example

Figure 7:
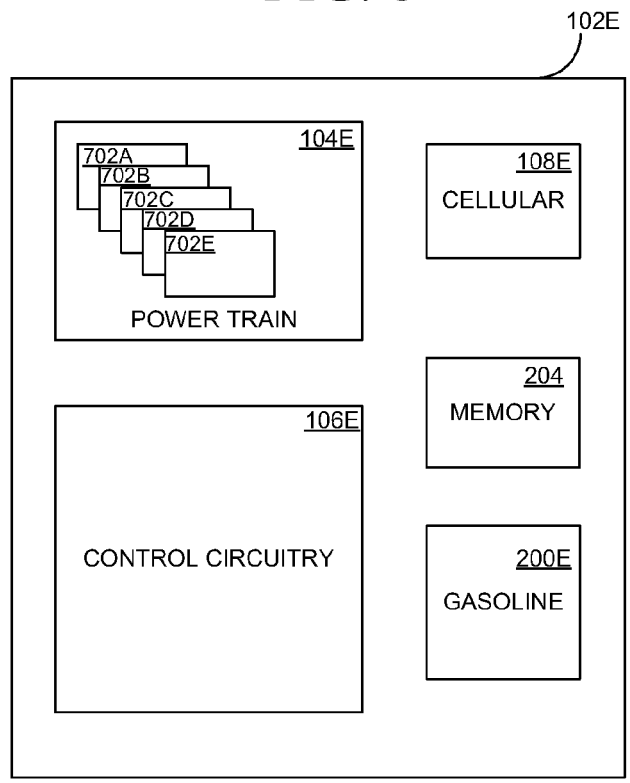
FIG. 7 is a block diagram of an automobile.

FIG. 7 is an example block diagram where the abstract components of the device 102 as depicted in FIGS. 1 and 2 are given exemplary detail. In the example, the device 102 is an automobile 102E. It is to be understood that the example provided here is not limiting and automobiles may incorporate various components, systems, and functionality that is not necessarily specified here with particularity.

A power train system 104E (e.g., the output module 104) includes an engine, transmission, wheels, and other componentry well known in the art. In various examples, a cellular communication module 108E (e.g., the communication module 108) includes an antenna and cellular chipset configured to communicate via a cellular network. In various examples, control circuitry 106E (e.g., the controller 106), such as processors, controllers and the like for controlling various aspects of the operation of the automobile 102E, is operatively coupled to the power train system 104E and cellular module 108E. In various examples, the automobile 102E includes a gasoline tank 200E for providing motive power (e.g., the power source 200).

In the example of the automobile 102E, the functions 702 include motive power 702A, audio 702B, climate control 702C, lighting 702D, and satellite navigation 702E, among other functions that may be incorporated in an automobile 102E. In an exemplary use case, the user of the automobile 102E may obtain the automobile 102E as a loan with an attendant condition of conveyance of a maintenance condition, including a maintenance procedure of changing the engine oil and of doing so on a maintenance schedule of not greater than every five thousand (5,000) miles or six (6) months.

In an exemplary, non-limiting use case, the automobile 102E transmits mileage information to the system 100 in general via the cellular module 108E. In certain examples, the automobile 102E further transmits information related to the engine oil, such as oil level and mileage and time since the engine oil was last replaced. In alternative examples, when the engine oil is changed, such as at a mechanic's shop, information related to having changed the oil is entered into the system 100, such as via the control device 110 or the remote device 118.

In an example, the condition module 128 receives information that the automobile 102E has traveled five thousand five hundred (5,500) miles and does not have information that the engine oil has been changed. The condition module 128 transmits condition status information indicating that the engine oil is overdue for changing. The remote device 118 transmits the condition status information to the automobile 102E. In an example, until the engine oil is at least one thousand (1,000) miles overdue, a verbal warning is displayed on a user interface of the automobile 102E. Upon the condition module 128 obtaining information that the automobile 102E has exceeded six thousand (6,000) miles, the remote device 118 transmits condition status information indicating that the automobile is more than one thousand (1,000) miles overdue. Upon receiving the condition status information, the control circuitry 106E commands the power train system 104E to shut down the motive power function 702A. In such an example, the remaining functions 702B-E may remain enabled as their function may not pertain to the power train system 104E. In various examples, the logic module 208 may delay disabling or impairing the motive power function 702A until the automobile 102E is not in operation, i.e., the automobile 102E is not, for instance, actively in use and shutting down the motive power function 702A may not result in the automobile 102E losing power on a road or in an undesirable location.

It is noted and emphasized that the maintenance status may not be based on whether the maintenance performance actually has occurred. Rather, the maintenance status may be based on whether the system 100 as a whole has condition status information that the maintenance has or has not occurred. In various examples, the system 100 is sensitive to reports that the maintenance has occurred and many not have sensitivity to methods of empirically determining that maintenance has occurred.

It is to be emphasized and understood that the example use cases disclosed herein may be applied to any of a variety of medical devices 102, both in terms of the actions taken and the components utilized.

Flowcharts

Figure 8:
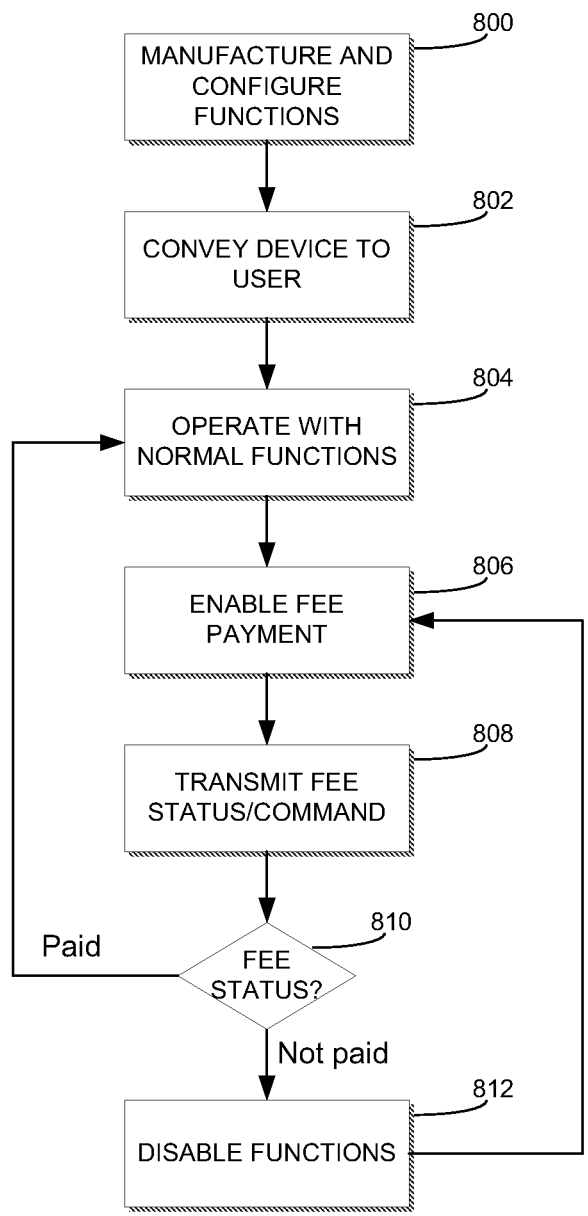
FIG. 8 is a flowchart for conducting payment-based device operation.

FIG. 8 is a flowchart for payment status-based device operation. The flowchart may relate in particular to a payment status, such as an ongoing payment status, of the device 102 as paid to a third party maintainer of the device 102, such as a third party providing maintenance for the device 102, such as in the form of follow ups of the device 102. While the flowchart is detailed in relation to the system 100 disclosed herein, it is to be understood that the flowchart may be applied to any applicable system and/or devices. Further, while the flowchart is detailed with respect to a payment status, it is to be understood that any condition status may be similarly applied pursuant to the steps of the flowchart.

At 800, the device 102 is manufactured and initially configured by the manufacturer of the device 102. The configuration of the device 102 may establish a normal or baseline set of functions 202.

At 802, the device 102 is conveyed to a user, such as a professional who may further update the normal or initial set of functions 202, or to the end user of the device 102. The cost to purchase the device 102 may be related to the conveyance of the device 102 at 802.

At 804, the device 102 optionally operates based on the initial set of functions 202. Installment payments for the purchase price or lease, maintenance, or subscription payments related to the operation of the device 102 may be accrued based on the operation at 804.

At 806, the payment module 128 enables making payments related to the ongoing operation of the device 102. The payments may be executed based on methodologies disclosed herein.

At 808, a device 110, 118 of the system 100 that is communicatively coupled to the payment module 128 or of which the payment module 128 is a component provides information related to the payment status of the device 102, such as at least one of a payment status or a payment status-related command or piece of information to the device 102. The payment status as transmitted to the device 102 may be an updated payment status over a previous payment status and may reflect that the payment has or has not been paid, or may reflect how much of the payment has been paid. The payment status-related command may provide an instruction to the device 102 on what functions 202 should be provided given the payment that was received by the payment module 128. The payment status or command may be received by the communication module 108 and stored in the memory module 204.

At 810, the controller 106 checks the payment status or payment status related information or command upon the lapsing of the period of time to make the payment or upon the triggering of an event, such as receiving the payment status information or command. The payment status information or command may have been stored in the memory module 204. If the payment status indicates that the payment has been made, the device 102 returns to step 804 and operates with normal functions 202.

At 812, if the payment status indicates that the payment has not been made, or the command indicates that functions 202 should be disabled or impaired, functions 202 are disabled or impaired as appropriate given the payment status and any other considerations as incorporated by the logic module 208. Upon disabling or impairing functions 202, the device 102 and the system 100 generally returns to step 806 and awaits payment.

Figure 9:
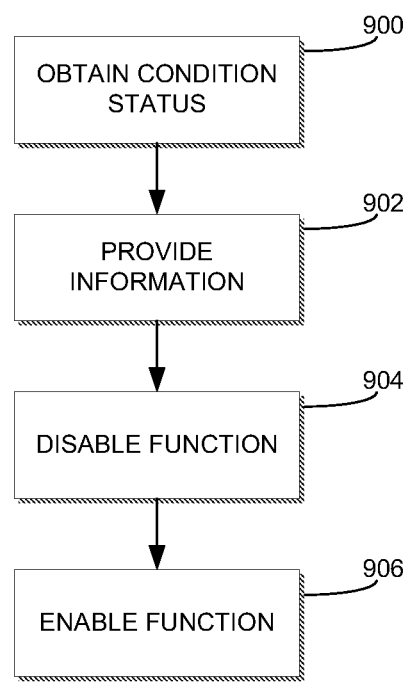
FIG. 9 is a flowchart for condition status-based device operation.

FIG. 9 is a flowchart for condition status-based device operation. The condition status may be based on a condition of conveyance. The flowchart may relate in particular to a payment status, such as an ongoing payment status, of the device 102 as paid to a third party maintainer of the device 102, such as a third party providing maintenance for the device 102, such as in the form of checkups of the device 102. While the flowchart is detailed in relation to the system 100 disclosed herein, it is to be understood that the flowchart may be applied to any applicable system and/or devices. Further, while the flowchart is detailed with respect to a payment status, it is to be understood that any non-physiologic condition status may be similarly applied pursuant to the steps of the flowchart.

At 900, a condition status is obtained based on a condition of conveyance of the device 102. Additionally, the system 100 may determine whether the condition of conveyance is such that the device 102 should be controlled. In an example, the condition of conveyance is a payment condition having a payment status based, at least in part, on a payment amount and a payment schedule. In an example, the function 202 is disabled or impaired based on the payment status indicating that the payment amount has not been paid according to the payment schedule. In an example, the payment status is based, at least in part, on at least one of an installment plan, a lease, a subscription, and a maintenance plan.

In an example, the condition of conveyance is a maintenance condition having a maintenance status based, at least in part, on a maintenance schedule and a maintenance procedure. In an example, the maintenance status is based on an indication of the maintenance procedure having been performed according to the maintenance schedule. In an example, the maintenance procedure relates to maintaining the function.

In an example, the function is one of a plurality of functions 202, wherein the output is delivered corresponding to the plurality of functions 202. In an example, ones of the plurality of functions 202 are selectively disabled or impaired based on the condition of conveyance of the device 102. In an example, upon selectively disabling or impairing ones of the plurality of functions 202, the device 102 does not deliver the output corresponding to the selectively disabled or impaired functions 202.

At 902, information related to the condition status of the device 102 is provided, wherein the information is configured to cause the device 102 to disable or impair the function 202 based on the condition status, wherein, upon disabling or impairing the function 202, the device 102 does not deliver the output corresponding to the function 202.

At 904, the function 202 is disabled or impaired based, at least in part, on the information related to the condition status. Stated differently, the device 102 is controlled consistent with the condition of conveyance and/or the condition status.

At 906, updated information is provided related to the condition status of the device 102, wherein the updated information is configured to cause the device 102 to enable a previously the function 202 based on an updated condition status, wherein, upon enabling the function 202, the device 102 delivers the output corresponding to the function 202. In an example, the function 202 is enabled upon the updated payment status indicating that the payment amount has been paid.

Block Diagram

Figure 10:
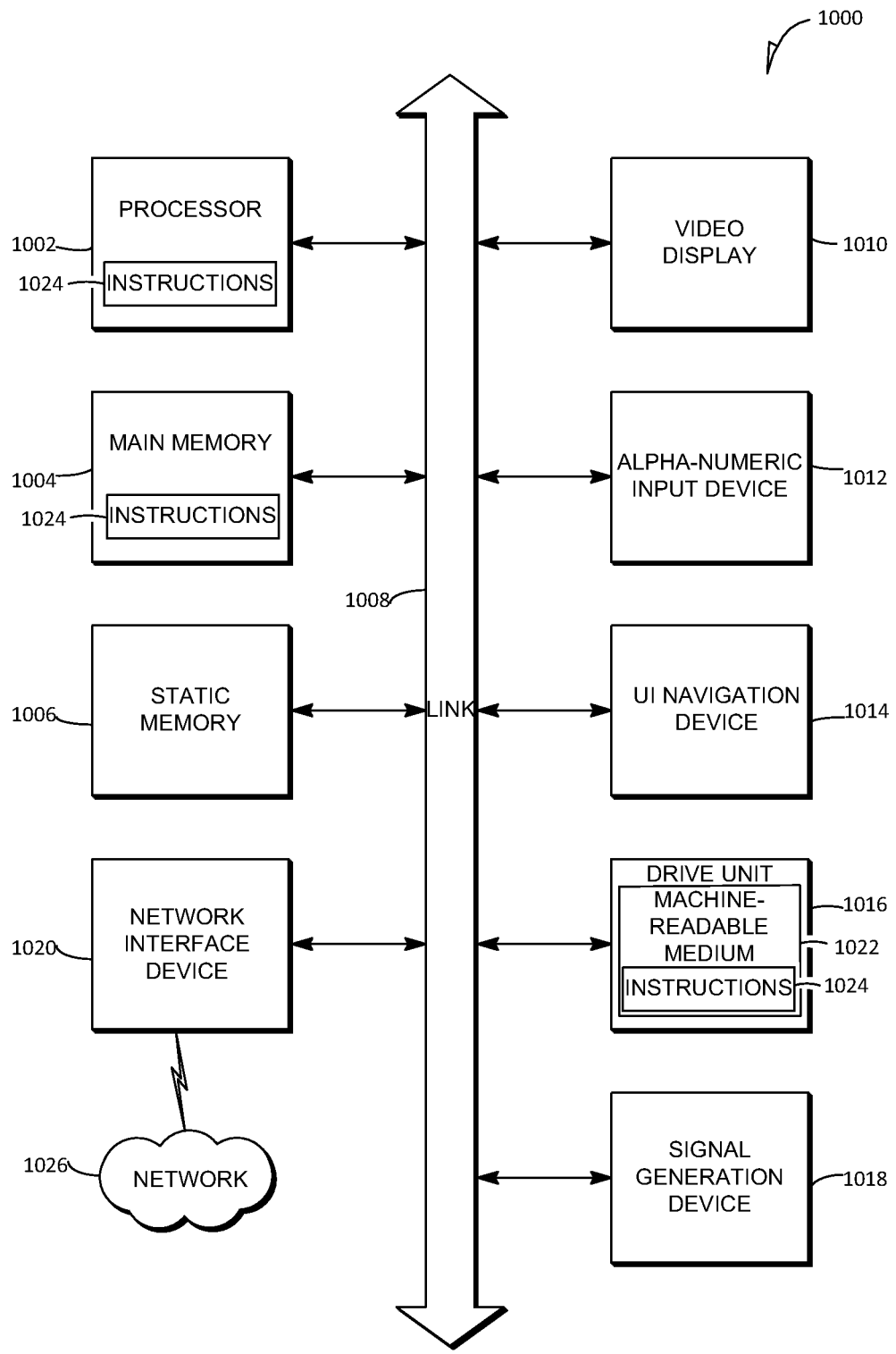
FIG. 10 is a block diagram of an electronic device.

FIG. 10 is a block diagram illustrating components of a machine 1000, according to some examples, able to read instructions from a machine-readable medium (e.g., a machine-readable storage medium) and perform any one or more of the methodologies discussed herein. Specifically, FIG. 10 shows a diagrammatic representation of the machine 1000 in the example form of a computer system and within which instructions 1024 (e.g., software) for causing the machine 1000 to perform any one or more of the methodologies discussed herein may be executed. In alternative examples, the machine 1000 operates as a standalone device or may be connected (e.g., networked) to other machines. In a networked deployment, the machine 1000 may operate in the capacity of a server machine or a client machine in a server-client network environment, or as a peer machine in a peer-to-peer (or distributed) network environment. The machine 1000 may be a server computer, a client computer, a personal computer (PC), a tablet computer, a laptop computer, a netbook, a set-top box (STB), a personal digital assistant (PDA), a cellular telephone, a smartphone, a web appliance, a network router, a network switch, a network bridge, or any machine capable of executing the instructions 1024, sequentially or otherwise, that specify actions to be taken by that machine. Further, while only a single machine is illustrated, the term "machine" shall also be taken to include a collection of machines that individually or jointly execute the instructions 1024 to perform any one or more of the methodologies discussed herein.

The machine 1000 includes a processor 1002 (e.g., a central processing unit (CPU), a graphics processing unit (GPU), a digital signal processor (DSP), an application specific integrated circuit (ASIC), a radio-frequency integrated circuit (RFIC), or any suitable combination thereof), a main memory 1004, and a static memory 1006, which are configured to communicate with each other via a bus 1008. The machine 1000 may further include a graphics display 1010 (e.g., a plasma display panel (PDP), a light emitting diode (LED) display, a liquid crystal display (LCD), a projector, or a cathode ray tube (CRT)). The machine 1000 may also include an alphanumeric input device 1012 (e.g., a keyboard), a cursor control device 1014 (e.g., a mouse, a touchpad, a trackball, a joystick, a motion sensor, or other pointing instrument), a storage unit 1016, a signal generation device 1018 (e.g., a speaker), and a network interface device 1020.

The storage unit 1016 includes a machine-readable medium 1022 on which is stored the instructions 1024 (e.g., software) embodying any one or more of the methodologies or functions described herein. The instructions 1024 may also reside, completely or at least partially, within the main memory 1004, within the processor 1002 (e.g., within the processor's cache memory), or both, during execution thereof by the machine 1000. Accordingly, the main memory 1004 and the processor 1002 may be considered as machine-readable media. The instructions 1024 may be transmitted or received over a network 1026 via the network interface device 1020.

As used herein, the term "memory" refers to a machine-readable medium able to store data temporarily or permanently and may be taken to include, but not be limited to, random-access memory (RAM), read-only memory (ROM), buffer memory, flash memory, and cache memory. While the machine-readable medium 1022 is shown in an example to be a single medium, the term "machine-readable medium" should be taken to include a single medium or multiple media (e.g., a centralized or distributed database, or associated caches and servers) able to store instructions. The term "machine-readable medium" shall also be taken to include any medium, or combination of multiple media, that is capable of storing instructions (e.g., software) for execution by a machine (e.g., machine 1000), such that the instructions, when executed by one or more processors of the machine (e.g., processor 1002), cause the machine to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" shall accordingly be taken to include, but not be limited to, one or more data repositories in the form of a solid-state memory, an optical medium, a magnetic medium, or any suitable combination thereof.

EXAMPLES

In Example 1, a device, system or method as disclosed here may control a function of a medical device based on a condition status, such as a payment status, of the medical device. Information related to a payment status may be provided to the medical device, wherein the information is configured to cause the medical device to deliver an output corresponding to the function. Updated payment status of the medical device may be obtained. Information related to the updated payment status of the medical device may be provided, wherein the information is configured to cause the medical device to disable or impair the function based on the payment status, wherein, upon disabling or impairing the function, the medical device does not deliver the output corresponding to the function.

In Example 2, the method of Example 1 may optionally further include that the payment status and the updated payment status are based, at least in part, on a payment amount and a payment schedule.

In Example 3, the method of any one or more of Examples 1 and 2 may optionally further include that the function is disabled or impaired based on the updated payment status indicating that the payment amount has not been paid according to the payment schedule.

In Example 4, the method of any one or more of Examples 1-3 may optionally further include enabling the function upon the updated payment status indicating that the payment amount has been paid.

In Example 5, the method of any one or more of Examples 1-4 may optionally further include that the function is one of a plurality of functions, wherein the output is delivered corresponding to the plurality of functions, wherein ones of the plurality of functions are selectively disabled or impaired based on the updated payment status, and wherein, upon selectively disabling or impairing ones of the plurality of functions, the medical device does not deliver the output corresponding to the selectively disabled or impaired functions.

In Example 6, the method of any one or more of Examples 1-5 may optionally further include that the updated payment status is based, at least in part, on a payment amount based on the plurality of functions.

In Example 7, the method of any one or more of Examples 1-6 may optionally further include that the function is an initially enabled function, and wherein the function is one of a plurality of functions, at least one of the plurality of functions being disabled or impaired, and further may optionally further include providing instructions to the medical device configured to enable a disabled or impaired one of the plurality of functions, wherein the output corresponds to the functions as enabled, and wherein the updated payment status is based, at least in part, on a payment amount corresponding to the functions as enabled.

In Example 8, the method of any one or more of Examples 1-7 may optionally further include that the payment status and the updated payment status are based on an installment payment plan based on an original purchase of the medical device and an installment payment schedule.

In Example 9, the method of any one or more of Examples 1-8 may optionally further include that disabling or impairing the function comprises disabling or impairing essentially all function of the medical device.

In Example 10, the method of any one or more of Examples 1-9 may optionally further include that the function is initially enabled at least one of prior to or upon conveyance of the medical device to the user.

In Example 11, a device, system or method may optionally include controlling a function of a medical device based on a condition status, such as a payment status, of the medical device. A payment module is configured to obtain payment information related to a payment related to the function of the medical device. A device, communicatively coupled to the payment module and the medical device, is configured to determine a payment status of the medical device and transmit function information to the medical device configured to disable or impaired the function based on the payment status, wherein, upon disabling or impairing the function, the medical device does not deliver the output corresponding to the function In Example 12, the system of Example 11 may optionally further include that the payment information at least one of whether a payment has been received and how much of a payment has been received.

In Example 13, the system of any one or more of Examples 11 and 12 may optionally further include that the payment information is a command to disable or impair the function.

In Example 14, the system of any one or more of Examples 11-13 may optionally further include that the payment status is based, at least in part, on a payment amount received by the payment module and a payment schedule.

In Example 15, the system of any one or more of Examples 11-14 may optionally further include that the function is disabled or impaired based on the payment status indicating that the payment amount has not been paid according to the payment schedule.

In Example 16, the method of any one or more of Examples 11-15 may optionally further include that the device is configured to transmit payment information to the medical device configured to enable the function upon the payment status indicating that the payment amount has been paid.

In Example 17, the system of any one or more of Examples 11-16 may optionally further include that the device is a control device, wherein the control device is communicatively coupled to the medical device via at least one of a wired link and a wireless link.

In Example 18, the system of any one or more of Examples 11-17 may optionally further include that wherein the device is a remote device, wherein the remote device is communicatively coupled to the medical device via a network connection.

In Example 19, the system of any one or more of Examples 11-18 may optionally further include that the device is configured to provide an indication related to the payment status to a user of at least one of the medical device and the device.

In Example 20, the system of any one or more of Examples 11-19 may optionally further include that the indication of the payment status is at least one of a visual indication on the device, an audio indication from the device, or an indication from the medical device.

In Example 21, a device, system or method may optionally include or utilize various components. An output module may be configured to deliver an output to a patient corresponding to a function. A controller, coupled to the output module, may be configured to enable the function based on an initial configuration of the medical device and disable or impair the function based on information relating to a condition status, such as a payment status, of the medical device, wherein, upon disabling or impairing the function, the output module does not deliver the output corresponding to the function.

In Example 22, the system of Example 21 may optionally further include that the information is the payment status.

In Example 23, the system of any one or more of Examples 21 and 22 may optionally further include that the information is a command to disable or impair the function.

In Example 24, the system of any one or more of Examples 21-23 may optionally further include that the payment status is based, at least in part, on a payment amount received by the payment module and a payment schedule.

In Example 25, the system of any one or more of Examples 21-24 may optionally further include that the function is disabled or impaired based on the payment status indicating that the payment amount has not been paid according to the payment schedule.

In Example 26, the method of any one or more of Examples 21-25 may optionally further include that the function is one of a plurality of functions, wherein the output is delivered corresponding to the plurality of functions, wherein the controller is configured to selectively disable or impair ones of the plurality of functions based on the payment status, and wherein, upon selectively disabling or impairing ones of the plurality of functions, the output module does not deliver the output corresponding to the selectively disabled or impaired functions.

In Example 27, the system of any one or more of Examples 21-26 may optionally further include a memory module configured to store the information related to the payment status.

In Example 28, the system of any one or more of Examples 21-27 may optionally further include a communication module configured to at least one of transmit and receive the information related to the payment status.

In Example 29, the system of any one or more of Examples 21-28 may optionally further include that the medical device is a hearing aid.

In Example 30, the system of any one or more of Examples 21-29 may optionally further include that disabling or impairing the function disables or impairs the operation of the hearing aid.

In Example 31, a device, system or method may optionally include controlling a function of a medical device based on a condition status, such as a payment status, of the medical device. A payment module is configured to obtain payment information related to a payment related to the function of the medical device. A processor, coupled to the payment module and the medical device, is configured to determine a payment status of the medical device based on the information related to the payment. A communication interface, coupled to the processor, is configured to transmit function information to the medical device, the function information being configured to disable or impair the function based on the payment status, wherein, upon disabling or impairing the function, the medical device does not deliver the output corresponding to the function.

In Example 32, the system of Example 31 may optionally further include that the payment information is the payment status.

In Example 33, the system of any one or more of Examples 31 and 32 may optionally further include that the payment information is a command to disable or impair the function.

In Example 34, the system of any one or more of Examples 31-33 may optionally further include that the payment status is based, at least in part, on a payment amount received by the payment module and a payment schedule.

In Example 35, the system of any one or more of Examples 31-34 may optionally further include that the function is disabled or impaired based on the payment status indicating that the payment amount has not been paid according to the payment schedule.

In Example 36, a device, system or method may optionally a processor, remote to a medical device, configured to generate information to control, at least in part, a function of the medical device based, at least in part, on a non-physiologic condition, and a transmitter, remote to the medical device, configured to transmit the information related to the non-physiologic condition to the medical device.

In Example 37, the system of Example 36 may optionally further include that the non-physiologic condition is a payment status of the medical device.

In Example 38, the system of any one or more of Examples 36 and 37 may optionally further include that the payment status of the medical device is based, at least in part, on a payment amount and a payment schedule.

In Example 39, the system of any one or more of Examples 36-38 may optionally further include that the function is disabled or impaired based on the updated payment status indicating that the payment amount has not been paid according to the payment schedule.

In Example 40, the system of any one or more of Examples 36-39 may optionally further include that the non-physiologic condition is a follow up status of the medical device.

In Example 41, the system of any one or more of Examples 36-40 may optionally further comprise a device remote to the medical device, wherein the device includes the processor and the transmitter.

In Example 42, the system of any one or more of Examples 36-41 may optionally further include that the function of the medical device is an output to the patient, and wherein the processor is configured to control the function by disabling or impairing the function.

In Example 43, the system of any one or more of Examples 36-42 may optionally further include that the function is one of a plurality of functions of the medical device and wherein the processor is configured to selectively control ones of the plurality of functions.

In Example 44, the system of any one or more of Examples 36-43 may optionally further include that the processor is configured to control the function by enabling the function.

In Example 45, the system of any one or more of Examples 36-43 may optionally further include that the function as enabled was a previously disabled or impaired function.

In Example 46, a device, system or method may optionally include a processor, remote to a device, configured to generate information to control, at least in part, a function of the device based, at least in part, on a condition of conveyance of the device, and a transmitter, remote to the device, configured to transmit the information related to the condition of conveyance to the device.

In Example 47, the system of Example 46 may optionally further include that the condition of conveyance is a payment status of the medical device.

In Example 48, the system of any one or more of Examples 46 and 47 may optionally further include that the payment status of the medical device is based, at least in part, on a payment amount and a payment schedule.

In Example 49, the system of any one or more of Examples 46-48 may optionally further include that the function is disabled or impaired based on the updated payment status indicating that the payment amount has not been paid according to the payment schedule.

In Example 50, the system of any one or more of Examples 46-49 may optionally further include that the condition of conveyance is a maintenance status of the device.

In Example 51, the system of any one or more of Examples 46-50 may optionally further include that the maintenance status is based on a maintenance requirement having been met.

In Example 52, the system of any one or more of Examples 46-51 may optionally further include that the information is a command configured to control the function of the device.

In Example 53, the system of any one or more of Examples 46-52 may optionally further include that the information is data relating to a current status of the condition of conveyance.

In Example 54, the system of any one or more of Examples 46-53 may optionally further include that the function of the device is an output, and wherein the processor is configured to control the function by disabling or impairing the function.

In Example 55, the system of any one or more of Examples 46-54 may optionally further include that the function is one of a plurality of functions of the medical device and wherein the processor is configured to selectively control ones of the plurality of functions.

In Example 56, a device, system or method may optionally include obtaining a condition status based on a condition of conveyance of the device and providing information related to the condition status of the device, wherein the information is configured to cause the device to disable or impair the function based on the condition status, wherein, upon disabling or impairing the function, the device does not deliver the output corresponding to the function.

In Example 57, the method of Example 56 may optionally further include that the condition of conveyance is a payment condition having a payment status based, at least in part, on a payment amount and a payment schedule.

In Example 58, the method of any one or more of Examples 56 and 57 may optionally further include that the function is disabled or impaired based on the payment status indicating that the payment amount has not been paid according to the payment schedule.

In Example 59, the method of any one or more of Examples 56-58 may optionally further include enabling the function upon the updated payment status indicating that the payment amount has been paid.

In Example 60, the method of any one or more of Examples 56-59 may optionally further include that the payment status is based, at least in part, on at least one of an installment plan, a lease, a subscription, and a maintenance plan.

In Example 61, the method of any one or more of Examples 56-60 may optionally further include that the condition of conveyance is a maintenance condition having a maintenance status based, at least in part, on a maintenance schedule and a maintenance procedure.

In Example 62, the method of any one or more of Examples 56-61 may optionally further include that the maintenance status is based on an indication of the maintenance procedure having been performed according to the maintenance schedule.

In Example 63, the method of any one or more of Examples 56-62 may optionally further include that the maintenance procedure relates to maintaining the function.

In Example 64, the method of any one or more of Examples 56-63 may optionally further include that the function is one of a plurality of functions, wherein the output is delivered corresponding to the plurality of functions, wherein ones of the plurality of functions are selectively disabled or impaired based on the condition of conveyance of the device, and wherein, upon selectively disabling or impairing ones of the plurality of functions, the device does not deliver the output corresponding to the selectively disabled or impaired functions.

In Example 65, the method of any one or more of Examples 56-64 may optionally further include providing updated information related to the condition status of the device, wherein the updated information is configured to cause the device to enable a previously the function based on an updated condition status, wherein, upon enabling the function, the device delivers the output corresponding to the function.

In Example 66, a device, system or method may optionally include obtaining a condition status based on a condition of conveyance of the device and providing information related to the condition status of the device, wherein the information is configured to cause the device to disable or impair the function based on the condition status, wherein, upon disabling or impairing the function, the device does not deliver the output corresponding to the function.

In Example 67, the device of Example 66 may optionally further include that the condition of conveyance is a payment condition having a payment status based, at least in part, on a payment amount and a payment schedule.

In Example 68, the device of any one or more of Examples 66 and 67 may optionally further include that the function is disabled or impaired based on the payment status indicating that the payment amount has not been paid according to the payment schedule.

In Example 69, the device of any one or more of Examples 66-68 may optionally further include enabling the function upon the updated payment status indicating that the payment amount has been paid.

In Example 70, the device of any one or more of Examples 66-69 may optionally further include that the payment status is based, at least in part, on at least one of an installment plan, a lease, a subscription, and a maintenance plan.

In Example 71, the device of any one or more of Examples 66-70 may optionally further include that the condition of conveyance is a maintenance condition having a maintenance status based, at least in part, on a maintenance schedule and a maintenance procedure.

In Example 72, the device of any one or more of Examples 66-71 may optionally further include that the maintenance status is based on an indication of the maintenance procedure having been performed according to the maintenance schedule.

In Example 73, the device of any one or more of Examples 66-72 may optionally further include that the maintenance procedure relates to maintaining the function.

In Example 74, the device of any one or more of Examples 66-73 may optionally further include that the function is one of a plurality of functions, wherein the output is delivered corresponding to the plurality of functions, wherein ones of the plurality of functions are selectively disabled or impaired based on the condition of conveyance of the device, and wherein, upon selectively disabling or impairing ones of the plurality of functions, the device does not deliver the output corresponding to the selectively disabled or impaired functions.

In Example 75, the device of any one or more of Examples 66-74 may optionally further include providing updated information related to the condition status of the device, wherein the updated information is configured to cause the device to enable a previously the function based on an updated condition status, wherein, upon enabling the function, the device delivers the output corresponding to the function.

In Example 76, the device of any one or more of Examples 66-76 may optionally further include that the device is at least one of a medical device, a consumer electronic device, an appliance, and a machine.

In Example 77, a device, system or method may optionally include a system comprising a device having controllable operations and a controller for controlling at least one of the controllable operations based, at least in part, on a condition of conveyance associated with the device.

In Example 78, the system of Example 77 may optionally further include that the controller is remote to the device.

In Example 79, the system of any one or more of Examples 77 and 78 may optionally further include that the controller is internal to the device.

In Example 80, the system of any one or more of Examples 77-79 may optionally further include that the device and the controller include circuitry permitting wireless communication between the device and the controller.

In Example 81, the system of any one or more of Examples 77-80 may optionally further include that the device and the controller are adapted to communicate by direct electronic connection.

In Example 82, a device, system or method may optionally include a method for controlling a device based on the status of a condition of conveyance, comprising determining whether the condition of conveyance is such that the device should be controlled and controlling the device consistent with the condition of conveyance.

In Example 83, the method of Example 82 may optionally further include that the condition of conveyance is a payment condition having a payment status based, at least in part, on a payment amount and a payment schedule.

In Example 84, the method of any one or more of Examples 82 and 83 may optionally further include that the device is controlled by at least one of disabling and impairing a function of the device based on the payment status indicating that the payment amount has not been paid according to the payment schedule.

In Example 85, the method of any one or more of Examples 82-84 may optionally further include that the payment status is based, at least in part, on at least one of an installment plan, a lease, a subscription, and a maintenance plan.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A method, comprising:
   obtaining, with a processor, via a network, a condition status of a hearing aid based on a condition of conveyance of the hearing aid;
   generating, with the processor, information related to the condition status of the hearing aid to a control device wherein the information is configured to cause the hearing aid to at least one of disable and impair a function of a plurality of functions of an amplifier of the hearing aid based on the condition status, wherein, upon disabling or impairing the function, the hearing aid does not deliver an audio output based on an ambient noise and corresponding to the function,
   wherein the audio output is delivered corresponding to the plurality of functions, wherein ones of the plurality of functions are selectively at least one of disabled and impaired based on the condition of conveyance of the hearing aid, and wherein, upon selectively disabling or impairing ones of the plurality of functions, the hearing aid does not deliver the audio output corresponding to the selectively disabled or impaired functions;
   wherein the condition of conveyance is a payment condition having a payment status based, at least in part, on a payment amount and a payment schedule, wherein the audio function is at least one of disabled and impaired based on the payment status indicating that the payment amount has not been paid according to the payment schedule; and
   enabling, with the processor, the audio function upon an updated payment status indicating that the payment amount has been paid.

2. The method of claim 1, wherein the condition of conveyance is a maintenance condition having a maintenance status based, at least in part, on a maintenance schedule and a maintenance procedure.

3. The method of claim 2, wherein the maintenance status is based on an indication of the maintenance procedure having been performed according to the maintenance schedule.

4. The method of claim 3, wherein the maintenance procedure relates to maintaining the function.

5. The method of claim 1, wherein the payment status is based, at least in part, on at least one of an installment plan, a lease, a subscription, and a maintenance plan.

6. A method, comprising:
   obtaining, with a processor, via a network, a condition status of a hearing aid based on a condition of conveyance of the hearing aid;
   generating, with the processor, information related to the condition status of the device, wherein the information is configured to cause the device to at least one of disable and impair the function based on the condition status, wherein, upon disabling or impairing the function, the device does not deliver an audio output of an amplifier of the hearing aid based on an ambient noise and corresponding to the function; and
   generating, with the processor, updated information related to the condition status of the hearing aid, wherein the updated information is configured to cause the hearing aid to enable a previously disabled or impaired function based on an updated condition status, wherein, upon enabling the function, the hearing aid delivers the audio output corresponding to the function;
   wherein the condition of conveyance is a payment condition having a payment status based, at least in part, on a payment amount and a payment schedule, wherein the function is at least one of disabled and impaired based on the payment status indicating that the payment amount has not been paid according to the payment schedule; and
   enabling the function upon an updated payment status indicating that the payment amount has been paid.

7. A hearing aid, comprising:
   an amplifier configured to deliver an audio output to a user based on an ambient noise and a function of the hearing aid;
   a controller configured to enable the function based on a condition of conveyance of the hearing aid;
   wherein at least one of disable and impair the function is based on information relating to a condition status of the hearing aid, the condition status being based on the condition of conveyance, wherein, upon disabling or impairing the function, the amplifier does not deliver the audio output corresponding to the function;

wherein the function is one of a plurality of functions of the hearing aid, wherein the audio output is delivered corresponding to the plurality of functions, wherein ones of the plurality of functions are selectively at least one of disabled and inhibited based on the condition of conveyance of the hearing aid, and wherein, upon selectively disabling or inhibiting ones of the plurality of functions, the amplifier does not deliver the output corresponding to the selectively disabled or inhibited functions; and wherein the condition of conveyance is a payment condition having a payment status based, at least in part, on a payment amount and a payment schedule, wherein the function is at least one of disabled and impaired based on the payment status indicating that the payment amount has not been paid according to the payment schedule;

wherein the controller is configured to enable the function upon an updated payment status indicating that the payment amount has been paid.

8. The hearing aid of claim 7, wherein the condition of conveyance is a maintenance condition having a maintenance status based, at least in part, on a maintenance schedule and a maintenance procedure.

9. The hearing aid of claim 8, wherein the maintenance status is based on an indication of the maintenance procedure having been performed according to the maintenance schedule.

10. The hearing aid of claim 9, wherein the maintenance procedure relates to maintaining the function.

11. The hearing aid of claim 7, wherein the payment status is based, at least in part, on at least one of an installment plan, a lease, a subscription, and a maintenance plan.

12. A hearing aid, comprising:
an amplifier configured to deliver an audio output to a user based on an ambient noise and a function of the hearing aid;
a controller configured to enable the function based on a condition of conveyance of the hearing aid, wherein at least one of disable and impair the function is based on information relating to a condition status of the hearing aid, the condition status being based on the condition of conveyance, wherein, upon disabling or impairing the function, the amplifier does not deliver the audio output corresponding to the function; and
a communication module configured to receive the information and updated information related to the condition status of the hearing aid, wherein the updated information is configured to cause the hearing aid to enable the function based on an updated condition status, wherein, upon enabling the function, the amplifier delivers the output corresponding to the function; and wherein the condition of conveyance is a payment condition having a payment status based, at least in part, on a payment amount and a payment schedule, wherein the function is at least one of disabled and impaired based on the payment status indicating that the payment amount has not been paid according to the payment schedule;

wherein the controller is configured to enable the function upon an updated payment status indicating that the payment amount has been paid.

13. The method of claim 6, wherein the payment status is based, at least in part, on at least one of an installment plan, a lease, a subscription, and a maintenance plan.

14. The method of claim 6, wherein the condition of conveyance is a maintenance condition having a maintenance status based, at least in part, on a maintenance schedule and a maintenance procedure.

15. The method of claim 14, wherein the maintenance status is based on an indication of the maintenance procedure having been performed according to the maintenance schedule.

16. The method of claim 15, wherein the maintenance procedure relates to maintaining the function.

17. The hearing aid of claim 12, wherein the payment status is based, at least in part, on at least one of an installment plan, a lease, a subscription, and a maintenance plan.

18. The hearing aid of claim 12, wherein the condition of conveyance is a maintenance condition having a maintenance status based, at least in part, on a maintenance schedule and a maintenance procedure.

19. The hearing aid of claim 18, wherein the maintenance status is based on an indication of the maintenance procedure having been performed according to the maintenance schedule.

20. The hearing aid of claim 19, wherein the maintenance procedure relates to maintaining the function.

* * * * *

UNITED STATES PATENT AND TRADEMARK OFFICE
CERTIFICATE OF CORRECTION

PATENT NO. : 9,460,431 B2  
APPLICATION NO. : 13/800810  
DATED : October 4, 2016  
INVENTOR(S) : Patrick J. Curry It is certified that error appears in the above-identified patent and that said Letters Patent is hereby corrected as shown below:

In the Claims

In Column 33, Line 63, in Claim 1, after "function,", delete "¶", therefor

Signed and Sealed this
Thirtieth Day of July, 2019

Andrei Iancu
*Director of the United States Patent and Trademark Office*